(12) United States Patent
Vago

(10) Patent No.: US 8,932,581 B2
(45) Date of Patent: Jan. 13, 2015

(54) CALCIUM-MEDIATED EFFECTS OF CORAL AND METHODS OF USE THEREOF

(75) Inventor: Razi Vago, Lehavim (IL)

(73) Assignee: Ben Gurion University of the Negev Research and Development Authority, Beer Sheva (IL)

( * ) Notice: Subject to any disclaimer, the term of this patent is extended or adjusted under 35 U.S.C. 154(b) by 780 days.

(21) Appl. No.: 12/743,812

(22) PCT Filed: Nov. 18, 2008

(86) PCT No.: PCT/IL2008/001511
§ 371 (c)(1),
(2), (4) Date: Mar. 7, 2011

(87) PCT Pub. No.: WO2009/066283
PCT Pub. Date: May 28, 2009

(65) Prior Publication Data
US 2011/0200563 A1    Aug. 18, 2011

Related U.S. Application Data

(60) Provisional application No. 60/996,450, filed on Nov. 19, 2007.

(51) Int. Cl.
A01N 63/00 (2006.01)
A61K 35/12 (2006.01)
A61K 35/28 (2006.01)
A61K 35/56 (2006.01)

(52) U.S. Cl.
CPC ............... *A61K 35/28* (2013.01); *A61K 35/614* (2013.01)
USPC ......................................... 424/93.7; 424/520

(58) Field of Classification Search
USPC ................................................ 424/93.7, 520
See application file for complete search history.

(56) References Cited

FOREIGN PATENT DOCUMENTS

| WO | 94/26322 A | 11/1994 |
|---|---|---|
| WO | 03/052084 A2 | 6/2003 |
| WO | 2005/025493 A2 | 3/2005 |

OTHER PUBLICATIONS

Peretz et al. Superior Survival and Durability of Neurons and Astrocytes on 3-Dimensional Aragonite Biomatrices; Tissue Engineering, vol. 13, No. 3 (2007) pp. 461-472.*

Petite et al. Tissue-Engineered Bone Regeneration; Nature Biotechnology, vol. 18 (2000) pp. 959-963.*

Tang et al. A Study on Repairing Mandibular Defect by Means of Tissue-Engineering and Human Bone Morphogenic Protein-2 Gene Transfection in Osteoporotic Rats; Zhonghua Kou Qiang Yi Xue Za Zhi, vol. 41, No. 7 (2006) pp. 430-431. downloaded from Pubmed http://www.ncbi.nlm.nih.gov/pubmed/17067463 on Feb. 14, 2013.*

Guillemin et al. Comparison of Coral Resorption and Bone Apposition With Two Natural Corals of Different Porosities; J. Biomed. Mater. Res., vol. 23, No. 7 (1989) pp. 765-779 (Abstract only) downloaded from Pubmed http://www.ncbi.nlm.nih.gov/pubmed/2738087 on Feb. 14, 2013.*

Abramovitch-Gottlib et al., "Biofabricated marine hydrozoan: A bioactive crystalline material prompting ossification of mesenchymal stem cells", Tissue Engineering, Apr. 2006, 12(4):729-739.

Birk et al., "Conversion of adipogenic to osteogenic phenotype using crystalline porous biomatrices of marine origin", Tissue Engineering, Jan. 2006, 12(1):121-131.

Gross-Aviv et al., "A study of crystalline biomaterials for articular cartilage bioengineering", Materials Science and Engineering C, Dec. 2008, 28(8):1388-1400.

Gross-Aviv et al., "The Role of Aragonite Matrix Surface Chemistry on the Chondrogenic Differentiation of Mesenchymal Stem Cells", Biomaterials, 2009, 30(5):770-779.

Vago et al., "Hard tissue remodeling using biofabricated coralline biomaterials", Journal of Biochemistry and Biophysical Methods, Jan. 2002, 50(2-3):253-259.

Di Carlo et al., "Biomaterial effects in articular cartiladge tissue engineering using polyglycolic acid, a novel marine origin biomaterial, IGF-I, and TGF-beta 1", Proceedings of the Institution of Mechanical Engineers, Part H, Journal of Engineering in Medicine, U.S. National Library of Medicine. Jan. 2009, 223(1):63-73.

International Search Report for PCT Application No. PCT/IL2008/001511, mailed Sep. 10, 2009, 7 pages.

* cited by examiner

*Primary Examiner* — Susan Hanley
*Assistant Examiner* — Paul Martin
(74) *Attorney, Agent, or Firm* — Kilpatrick Townsend & Stockton LLP

(57) ABSTRACT

This invention is directed to coral scaffolds seeded with precursor cells in culture in the presence of a chelator and uses thereof in inducing or enhancing bone and/or cartilage formation in a subject, and kits related thereto. This invention is also directed to use of cadherin-upregulating coral for treating cancer or inhibiting cancer progression. This invention is also directed to use of aragonite or calcite-producing species for in vivo calcium release, and its application to the treatment of skin diseases, disorders or conditions.

31 Claims, 5 Drawing Sheets

1- POR

2- GCPOR

Day 1     Day 4     Day 7

CALCIUM-MEDIATED EFFECTS OF CORAL AND METHODS OF USE THEREOF

CROSS REFERENCE TO RELATED APPLICATIONS

This application is a national phase entry of International Application Number PCT/IL2008/001511 filed Nov. 18, 2008, which claims the benefit of U.S. Provisional Application Number 60/996,450 filed Nov. 19, 2007. Each aforelisted priority application is hereby incorporated by reference in its entirety.

FIELD OF THE INVENTION

This invention is directed to coral scaffolds seeded with precursor cells in culture in the presence of a chelator and uses thereof in inducing or enhancing bone and/or cartilage formation in a subject, and kits related thereto. This invention is also directed to use of cadherin-upregulating coral for treating cancer or inhibiting cancer progression. This invention is also directed to use of aragonite or calcite-producing species for in vivo calcium release.

BACKGROUND OF THE INVENTION

Surgical intervention and grafting are sometimes necessary to restore mechanical function and reconstruct the morphology of bone resulting from trauma, tumors, or abnormal bone developments. Synthetic materials such as metals and bone cements have also been used for many years, but often result in stress-shielding to the surrounding bone and fatigue failure of the implant. Another possibility is autologous bone grafting, although the supply of autologous bone tissue is limited and its collection is painful, with the risk of infection, hemorrhage, cosmetic disability, nerve damage, and loss of bone function. In addition, significant morbidity is associated with autograft harvest sites. These problems may be overcome by engineering tissue using scaffolds made of synthetic or natural biomaterials that promote the adhesion, migration, proliferation, and differentiation of bone marrow stem cells, also known as mesenchymal stem cells (MSCs). An association between biocomponents and biologic regenerative and repair responses can be promoted by providing a scaffold containing spaces morphologically compatible with osteons and their vascular interconnections.

The immediate microenvironment and the three-dimensional (3D) organization are important factors in differentiation in general and particularly in osteogenic differentiation.

Some bone tissue engineering scaffolds consists of natural polymers, such as collagen, alginate, hyaluronic acid, and chitosan. Natural materials offer the advantages of specific cell interaction, easy seeding of cells because of their hydrophilic interactions, low toxicity and low chronic inflammatory response. However, these scaffolds often are mechanically unstable and do not readily contribute to the creation of tissue structures with a specific predefined shape for transplantation. To obtain mechanical strength, chemical modification is required, which may lead to toxicity.

While most candidate materials must be synthetically modified to meet the essential requirements of an adequate bone and/or cartilage substitute, this is not necessarily the case for Marine skeletal material, such as natural coral exoskeletons. Calcified sessile and free-living organisms harbor a wide array of nanoscale to mesoscale modularly organized skeletal materials.

SUMMARY OF THE INVENTION

In one embodiment, the present invention provides a method of inducing or enhancing bone and/or cartilage formation in a subject comprising administering to said subject a composition comprising coral, wherein said coral is seeded with a precursor cell in culture in the presence of a chelator for a period of time sufficient to seed said precursor cell in said coral. In another embodiment, the present invention provides a kit for bone and/or cartilage formation comprising coral, bone precursor or stem cells, and a calcium chelator.

In another embodiment, the present invention provides a method of treating cancer or inhibiting cancer progression comprising contacting a neoplastic, pre-neoplastic, or hyperplastic cell in a subject with a composition comprising coral, wherein said coral upregulates cadherin levels and wherein said coral is from the *Porites* or *Acropora* species.

In another embodiment, the present invention provides a method of preventing a relapse of cancer, reducing the incidence of cancer, prolonging the remission of cancer, or treating a precancerous precursor, the method comprising contacting a neoplastic, pre-neoplastic, or hyperplastic cell in a subject with a composition comprising coral, wherein said coral upregulates cadherin levels.

In another embodiment, the present invention provides a method of in vivo calcium release comprising contacting cells in a subject with an aragonite or calcite-producing species, whereby cells recruited to said aragonite or calcite promote calcium release from said aragonite or calcite.

DETAILED DESCRIPTION OF TILE PRESENT INVENTION

Figures 1A, 1B:
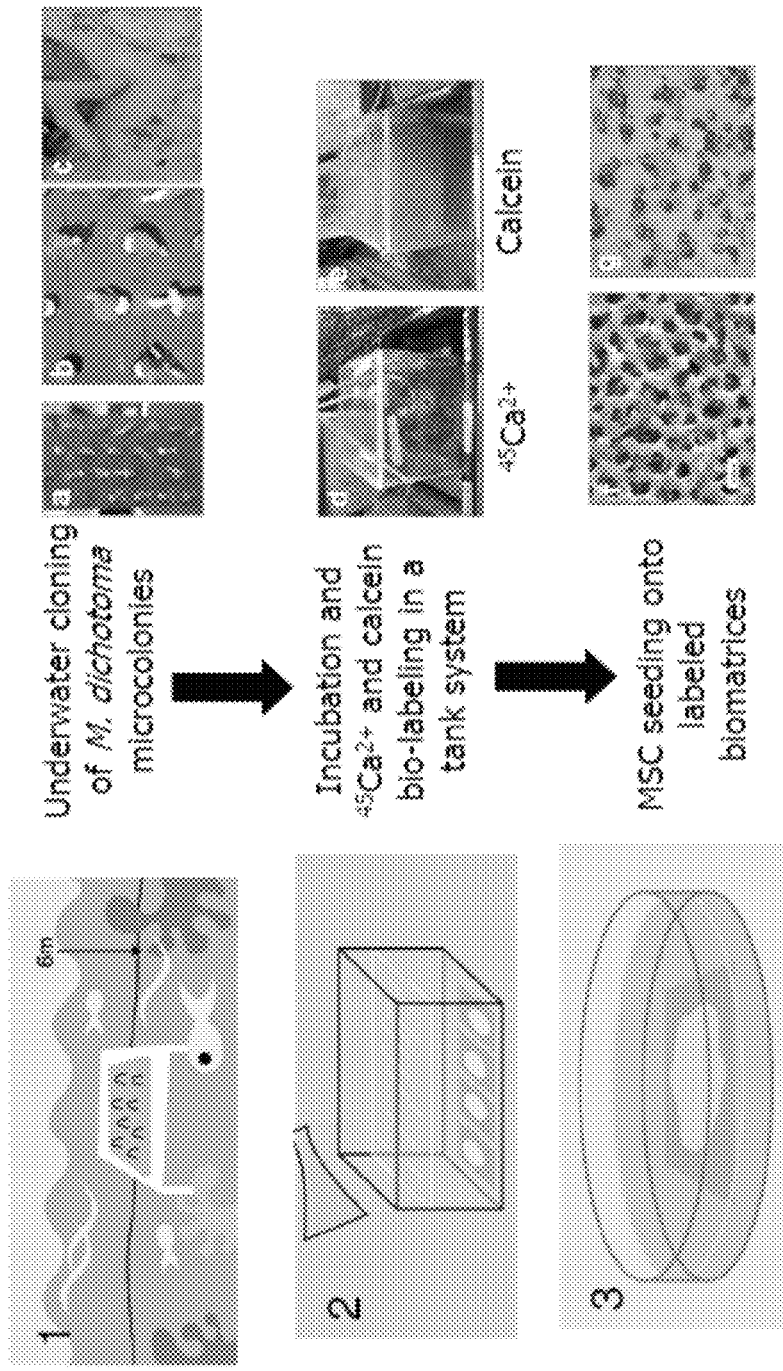
FIG. 1A is a schematic drawing of the biolabeling experiment. The experiment was performed in three steps: (1) underwater cloning of *M dichotoma* microcolonies, (2) incubation and biolabeling of microcolonies in a tank system and (3) MSCs seeding onto labeled biomatrices.
FIG. 1B presents photographs of the biolabeling steps represented in FIG. 2A. Tips of *M dichotoma* were cut, glued to glass slides and placed on P.V.C plates (a and b). The tips act as growing centers from which a porous thin layer of crystalline aragonite was established (c). Microcolonies were transferred to tank systems and incubated with $^{45}Ca^{2+}$ (d) and calcein (e) for 48 hours. Then, MSCs were seeded onto labeled biomatrices and cultured with low calcium or control medium. Photographs of the central area of porous aragonite biomatrix and crystals located on the sides/margins of biomatrix seeded with MSCs are shown in (f) and (g), respectively.

Coral, which is comprised of CaCO3 in the crystalline form of calcite, aragonite, and silicate SiO2 combined with Mg(OH)2, has the advantages of allowing fast cellular invasion, adherence, and proliferation. Surprisingly, it was found that coral, when contacted with cells in the presence of a chelator increased local mesenchymal stem cell density (Example 1, FIG. 2).

In one embodiment, the present invention is directed to use of coral seeded with a precursor cell in culture in the presence of a chelator for inducing or enhancing bone and/or cartilage formation in a subject and kits related thereto.

In one embodiment, the present invention provides a method of inducing or enhancing bone and/or cartilage formation in a subject comprising administering to said subject a composition comprising coral, wherein said coral is seeded with a precursor cell in Y in the presence of a chelator for a period of time sufficient to seed said precursor cell in said coral.

In some embodiments, the term bone and/or cartilage formation, or osteogenesis, refers to the creation of new bone and/or cartilage mass or the repair of fractures, including non-union fractures. In some embodiments, the process comprises new bone and/or cartilage structure growth or increased density of existing bone and/or cartilage. In one embodiment, bone and/or cartilage mass and/or fracture healing are assessed by histology, X-ray photographs, computerized X-ray densitometry, computerized fluorescence densitometry, or another method known in the art, or any combination thereof.

In one embodiment, the methods of this invention may be used to enhance bone and/or cartilage formation in a subject, wherein said subject may be, in one embodiment, a vertebrate, and in another embodiment, the vertebrate is a mammal, including domestic animals, such as pigs, cattle, horses, sheep and goats and also including pets such as dogs, cats and experimental mammals, such as rodents. In another embodiment, the subject is a human. In some embodiments, the subject is male or female. In some embodiments, the subject has osteoporosis or bone frailty or a cartilage defect.

In some embodiments, the subject has osteoarthritis, rheumatoid arthritis, aseptic necrosis, osteochondritis dissecans, articular cartilage injuries, chondromalacia patella, chondrosarcoma, chondrosarcoma-head and neck, costochondritis, enchondroma, hallux rigidus, hip labral tear, osteochondritis dissecans, torn meniscus, relapsing polychondritis, canine arthritis, fourth branchial arch defect or cauliflower ear. In one embodiment, methods of this invention induce or enhance cartilage repair in degenerative cartilagenous disorders comprising disorders characterized, at least in part, by degeneration or metabolic derangement of connective tissues of the body, including not only the joints or related structures, including muscles, bursae (synovial membrane), tendons, and fibrous tissue, but also the growth plate, meniscal system, and intervertebral discs.

In one embodiment, the methods of the present invention are useful for the regeneration of tissue of various types, including bone, cartilage, tendon, ligament, muscle, skin, and other connective tissue, as well as nerve, cardiac, liver, lung, kidney, pancreas, brain, and other organ tissues.

In one embodiment, the methods and kits employ use of a coral. In one embodiment, the coral comprise any species, including, inter alia, *Porites, Acropora, Millepora*, or a combination thereof.

In one embodiment, the coral is from the *Porites* species. In one embodiment, the coral is *Porites Lutea*. In most species, the void to solid ratios is generally in the range of 0.4 to 0.6, and the void phase completely interconnects, forming a highly regular network that interpenetrates the solid calcium carbonate phase. In one embodiment, this uniform and interconnecting architecture is particularly useful as a scaffold in the methods and kits of the instant invention.

In one embodiment, the coral is from the *Acropora* species. In one embodiment, the coral is *Acropora grandis*, which in one embodiment is very common, fast growing, and easy to grow in culture. Thus, in one embodiment *Acropora* samples can be easily collected in sheltered areas of the coral reefs and collection from the coral reefs can be avoided by use of cultured coral material.

The average skeletal density of *Acropora grandis* is ~2.7 g/cml. Because the skeleton of this coral species is dense and strong, it can be easily machined to a variety of configurations of shaped products or structures of different sizes, for example by grinding. This material is particularly suited for use in an implant device, in particular for load bearing bones where strength is an essential property of the implant device. Thus, in one embodiment, *Acropora* coral is useful as a scaffold in the methods and kits of the instant invention.

In another embodiment, the coral is from the *Millepora* species. In one embodiment, the coral is *Millepora dichotoma*. In one embodiment, the coral has a pore size of 150 μm and can be cloned and cultured, making *Millerpora* useful as a scaffold in the methods and kits of the instant invention, in one embodiment.

In another embodiment, the coral is from any one or more of the following species: *Favites halicora; Goniastrea retiformis; Acanthastrea echinata; Acanthastrea hemprichi; Acanthastrea ishigakiensis; Acropora aspera; Acropora austera; Acropora* sp. "brown digitate"; *Acropora carduus; Acropora cerealis; Acropora chesterfieldensis; Acropora clathrata; Acropora cophodactyla; Acropora* sp. "danai-like"; *Acropora divaricata; Acropora donei; Acropora echinata; Acropora efflorescens; Acropora gemmifera; Acropora globiceps; Acropora granulosa; Acropora* cf *hemprichi; Acropora kosurini; Acropora* cf *loisettae; Acropora longicyathus; Acropora loripes; Acropora* cf *lutkeni; Acropora paniculata; Acropora proximalis; Acropora rudis; Acropora selago; Acropora solitaryensis; Acropora* cf *spicifera* as per Veron; *Acropora* cf *spicifera* as per Wallace; *Acropora tenuis; Acropora valenciennesi; Acropora vaughani; Acropora vermiculata; Astreopora gracilis; Astreopora myriophthalma; Astreopora randalli; Astreopora suggesta; Australomussa rowleyensis; Coscinaraea collumna; Coscinaraea crassa; Cynarina lacrymalis; Distichopora violacea; Echinophyllia echinata; Echinophyllia* cf *echinoporoides; Echinopora gemmacea; Echinopora hirsutissima; Euphyllia ancora; Euphyllia divisa; Euphyllia yaeyamensis; Favia rotundata; Favia truncatus; Favites acuticollis; Favities pentagon; Fungia granulosa; Fungia klunzingeri; Fungia mollucensis; Galaxea acrhelia; Goniastrea edwardsi; Goniastea minuta; Hydnophora pilosa; Leptoseris explanata; Leptoseris incrustans; Leptoseris mycetoseroides; Leptoseris scabra;*

*Leptoseris yabei; Lithophyllon undulatum; Lobophyllia hemprichii; Merulina scabricula; Millepora dichotoma; Millepora exaesa; Millepora intricata; Millepora murrayensis; Millipora platyphylla; Monastrea curta; Monastrea colemani; Montipora caliculata; Montipora capitata; Montipora foveolata; Montipora meandrina; Montipora tuberculosa; Montipora* cf *vietnamensis; Oulophyllia laevis; Oxypora crassispinosa; Oxypora lacera; Pavona bipartita; Pavona venosa; Pectinia alcicornis; Pectinia paeonea; Platygyra acuta; Platygyra pini; Platygyra* sp "green"; *Platygyra verweyi; Podabacia* cf *lanakensis; Porites annae; Porites cylindrica; Porites evermanni; Porites monticulosa; Psammocora digitata; Psammocora explanulata; Psammocora haimeana; Psammocora superficialis; Sandalolitha dentata; Seriatopora caliendrum; Stylocoeniella armata; Stylocoeniella guentheri; Stylaster* sp.; *Tubipora musica; Turbinaria stellulata*; or any coral known in the art, or a combination thereof.

In another embodiment, coral for use in the methods of the present invention may be *Madreporaria, Helioporida* of the order Coenothecalia, *Tubipora* of the order Stolonifera, *Millepora* of the order Milleporina, or others known in the art.

In some embodiments, coral for use in the scaffolds, methods and/or kits of this invention may comprise scleractinian coral, including in some embodiments, Goniopora and others. In some embodiments, coral for use in the scaffolds, methods and/or kits of this invention may comprise Alveoppora. In some embodiments, coral for use in the scaffolds, methods and/or kits of this invention may comprise bamboo corals, including in some embodiments, coral from the family Isididae, genera Keratoisis, Isidella, and others.

The present invention encompasses use of coral as described herein for inducing or enhancing bone and/or cartilage formation. In one embodiment, coral may be administered in solid form. In another embodiment, coral may be administered locally which in one embodiment is directly to a site of bone and/or cartilage infirmity or to a site of desired bone and/or cartilage formation. In one embodiment, coral may be machined into a variety of configurations, and quite complex shapes such as cylindrical structures and threaded structures may be formed by appropriate machine processing. In another embodiment, coral may be administered in solid blocks, rods or granular forms. In one embodiment, coralline materials are shaped in such a way as to conform to the shape of existing bone and/or cartilage or to fill gap and contour defects in bone and/or cartilage. In one embodiment, coral is implanted in an orientation that allows it to contact the maximum surface area of an adjacent bone and/or cartilage. In another embodiment, coral is shaped so that it inserts into a non-union fracture.

In one embodiment, the size of coral scaffolds may be any size that would be useful for the purposes of the present invention, as would be known to one of skill in the Art depending on the purpose. For example and in one embodiment, the coral scaffold may be substantially the same size as the structure it is meant to replace, while in another embodiment, the scaffold or a portion thereof may be the size of a bone fissure or fracture such that it may be placed therein to enhance bone formation in a discrete location. In another embodiment, the average pore size of the coral is appropriate for the seeding of precursor cells, which in one embodiment, is 1 micron-1 mm, 50-500 microns, or in another embodiment, 150-220 microns.

In one embodiment, coral is washed, bleached, frozen, dried, or a combination thereof prior to seeding with precursor cells.

In one embodiment, the coral is seeded with a precursor cell. In one embodiment, the precursor cell is a mesenchymal stem cell. In other embodiments, the cell may be a mesenchymal cell; chondrocyte; fibrochondrocyte; osteocyte; osteoblast; osteoclast; synoviocyte; bone marrow cell; stromal cell; stem cell; embryonic stem cell; precursor cell, derived from adipose tissue; peripheral blood progenitor cell; stem cell isolated from adult tissue; genetically transformed cell; or a combination thereof. In another embodiment, a precursor cell may refer to a combination of chondrocytes and other cells; a combination of osteocytes and other cells; a combination of synoviocytes and other cells; a combination of bone marrow cells and other cells; a combination of mesenchymal cells and other cells; a combination of stromal cells and other cells; a combination of stem cells and other cells; a combination of embryonic stem cells and other cells; a combination of precursor cells isolated from adult tissue and other cells; a combination of peripheral blood progenitor cells and other cells; a combination of stem cells isolated from adult tissue and other cells; and a combination of genetically transformed cells and other cells.

In one embodiment of the present invention, the precursor cells for use in the method of the present invention are prepared from an organ tissue of the recipient mammal (i.e. autologous), or a syngeneic mammal. In another embodiment, allogeneic and xenogeneic precursor cells may be utilized.

In another embodiment, the precursor cells utilized for administration are prepared from a donor who is human leukocyte antigen (HLA)-matched with the recipient, where in one embodiment, HLA is the major histocompatibility complex in humans. In one embodiment, donor and recipient are matched for class I major histocompatibility complex (MHC) genes, class II MHC genes, or a combination thereof. In one embodiment, class I MHC genes comprise HLA-A, HLA-B, and HLA-C, wherein in one embodiment, a mismatch of class I MHC genes increases the risk of graft rejection, and in one embodiment, class II MHC genes comprise HLA-DPA1, HLA-DPB1, HLA-DQA1, HLA-DQB1, HLA-DRA, HLA-DRB1, wherein in one embodiment, a mismatch of class II MHC genes increases the risk of GVHD. In another embodiment, donor and recipient are matched for HLA-DM and HLA-DO genes.

The coral is seeded with precursor cells in the presence of a chelator. In one embodiment, the term chelator refers to a chelating agent or chelating reagent, which in one embodiment, comprises a calcium chelator. In one embodiment, the chelator may comprise: ethylenediamine-N,N,N',N'-tetraacetic acid (EDTA), O,O'-bis(2-aminophenylethyleneglycol)ethylenediamine-N,N,N,N-tetraacetic acid (BAPTA), N,N-bis(2-hydroxyethyl) glycine (Bicine), trans-1,2-diaminocyclohexane-ethylenediamine-N,N,N',N-tetraacetic acid (CyDTA), 1,3-diamino-2-hydroxypropane-ethylenediamine-N,N,N',N'-tetraacetic acid (DPTA-OH), diethylenetriamine-N,N,N',N''',N'''-pentaacetic acid (DPTA), ethylenediamine-N,N'-dipropionic acid dihydrochloride (EDDP), ethylenediamine-N,N'-bis(methylenephosphonic acid) hemihydrate (EDDPO), N-(2-hydroxyethyl)ethylenediamine-N,N',N'-triacetic acid (EDTA-OH), ethylenediamine-N,N,N',N'-tetrakis (methylenephosphonic acid) (EDTPO), O,O'-bis(2-aminoethyl)ethyleneglycol tetraacetic acid (EGTA), N,N'-bis(2-hydroxybenzyl)ethylenediamine-N,N-diacetic acid (ABED), 1,6-hexamethylenediamine-N,N,N', N'-tetraacetic acid (HDTA), N-(2-hydroxyethyl)iminodiacetic acid (HIDA), iminodiacetic acid (IDA), 1,2-diaminopropane-N,N,N',N'-tetraacetic acid (methyl-EDTA), nitrilotriacetic acid (NTA), nitrilotripropionic acid (NTP), nitrilotris(methylenephosphonic acid) trisodium salt (NTPO), N,N,N',N-tetrakis(2-pyridylmethyl)ethylenediamine (TPEN), and triethylenetetramine-N,N,N',N'',N''-hexaacetic acid (TTHA), rhod-2, DMSA, FLUO 3, FURA 2, INDO 1, QUIN 2, or other chelators known in the art, or a combination thereof. In another embodiment, a chelator is a zinc, manganese, magnesium, copper, iron, chelator, or a combination thereof. In one embodiment, a zinc chelator comprises ethylenediiminodi-2-pentanedioic acid, Zinquin, histidine, or the chelators described hereinabove, or a combination thereof.

In one embodiment, coral is seeded with a precursor cell in culture in the presence of a chelator for a period of time sufficient to seed said precursory cell in said coral. In one embodiment, coral is seeded with the precursor cell in serum-free medium. In another embodiment, the seeding is performed in low serum medium. In another embodiment, seeding is performed in a medium to which serum was added. In one embodiment, such serum-supplemented medium comprises 10% serum substitute supplement, 10% Fetal bovine serum (FBS or FCS), enriched calf serum, horse serum, goat serum, human serum, or a combination thereof.

By "cell culture" or "culture" is meant the maintenance of cells in an artificial, in vitro environment. It is to be understood, however, that the term "cell culture" is a generic term and may be used to encompass the cultivation not only of individual cells, but also of tissues, organs, organ systems or whole organisms, for which the terms "tissue culture," "organ culture," "organ system culture" or "organotypic culture" may occasionally be used interchangeably with the term "cell culture."

In one embodiment, media for cultivating or growing eukaryotic and/or prokaryotic cells, tissues, organs, etc, may be used to grow precursor cells of the present invention. Such media comprise Dulbecco's Modified Eagle's Medium (DMEM), Minimal Essential Medium (MEM), Basal Medium Eagle (BME), RPMI-1640, Ham's F-10, Ham's F-12, αMinimal Essential Medium (αMEM), Glasgow's Minimal Essential Medium (G-MEM), Iscove's Modified Dulbecco's Medium (IMDM), or a combination thereof. Other media that are commercially available (e.g., from Life Technologies, Inc.; Rockville, Md.) or that are otherwise known in the art may be equivalently used in accordance with the present invention including, but not limited to, 293 SFM, CD-CHO medium, VP SFM, BGJb medium, Brinster's BMOC-3 medium, cell culture freezing medium, CMRL media, EHAA medium, eRDF medium, Fischer's medium, Gamborg's B-5 medium, GLUTAMAX™ media, Grace's insect cell media, HEPES media, Richter's modified MEM, IPL-41 insect cell medium, Leibovitz's L-15 media, McCoy's 5A media, MCDB 131 medium, Media 199, Modified Eagle's Medium (MEM), Medium NCTC-109, Schneider's *Drosophila* medium, TC-100 insect medium, Waymouth's MB 752/1 media, William's Media E, protein free hybridoma medium II (PFHM II), AIM V media, Keratinocyte SFM, defined Keratinocyte SFM, STEMPRO® SFM, STEMPRO® complete methylcellulose medium, HepatoZYME-SFM, Neurobasal™ medium, Nerobasal-A medium, Hibernate™ A medium, Hibernate E medium, Endothelial SFM, Human Endothelial SFM, Hybridoma SFM, PFHM II, Sf 900 medium, Sf 900 II SFM, EXPRESS FIVE® medium, CHO-S-SFM, AMINOMAX-II complete medium, AMINOMAX-C 100 complete medium, AMINOMAX-C 100 basal medium, PB-MAX™ karyotyping medium, KARYOMAX bone marrow karyotyping medium, KNOCKOUT D-MEM and $CO_2$ independent medium.

Figure 2A:
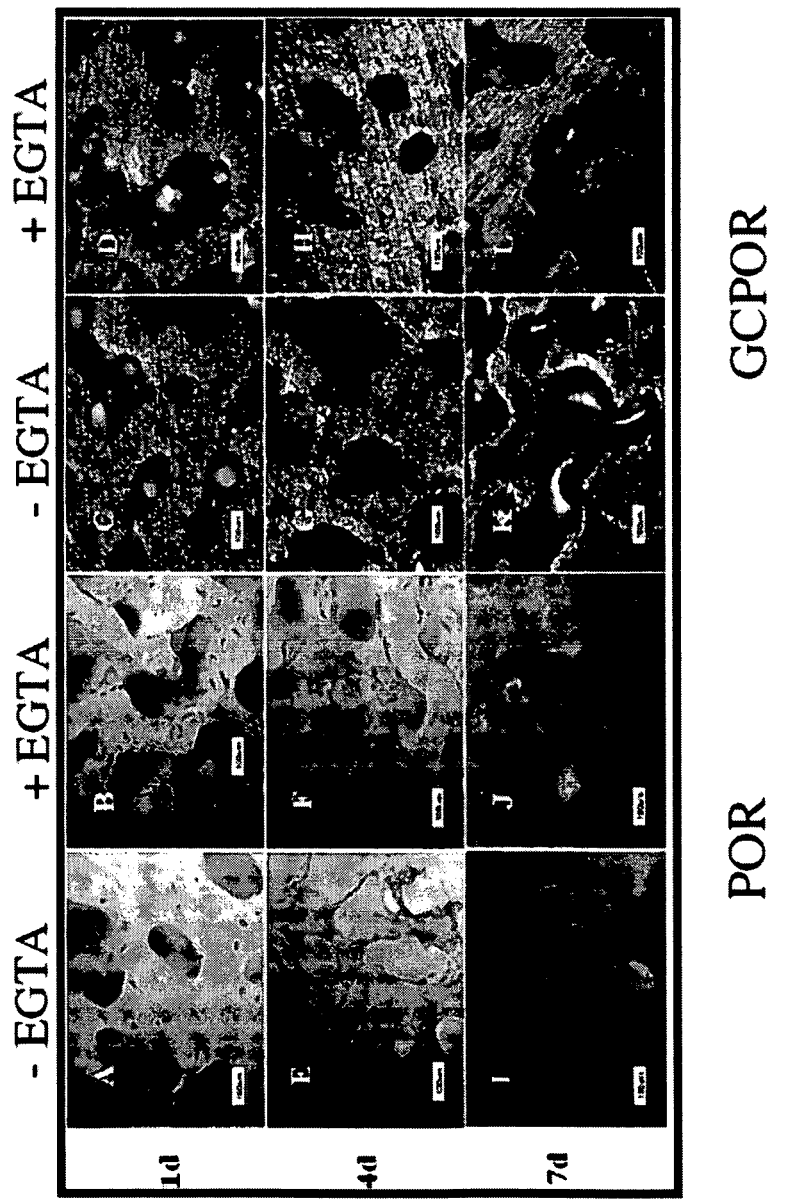
FIGS. 2A and 2B present Scanning Electron Micrographs (SEMs) showing cell distribution and density in porites lutea (POR) and gold-coated POR (GCPOR) biomatrices seeded with MSCs, at 1, 4, and 7 days post seeding. The effect of incubation with the calcium chelator, EGTA on cell distribution and density is also demonstrated. Scale bar=100 microns.
Figure 2B:
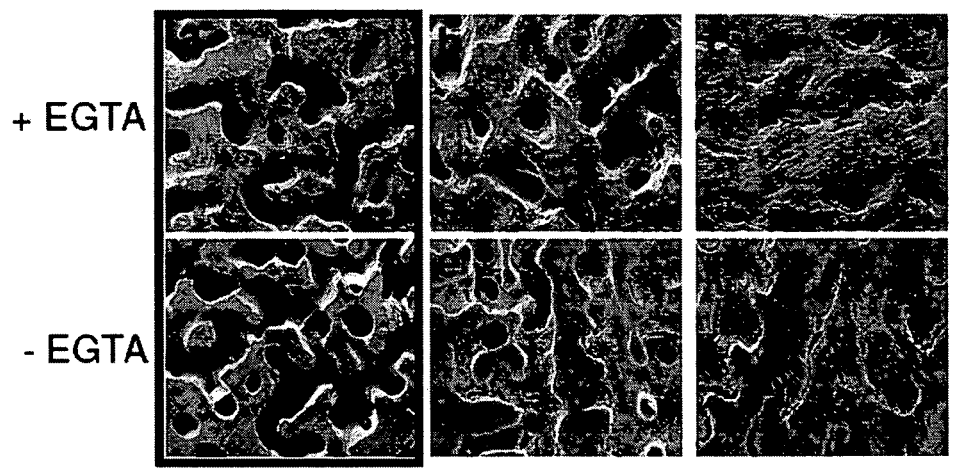
Figure 2B:
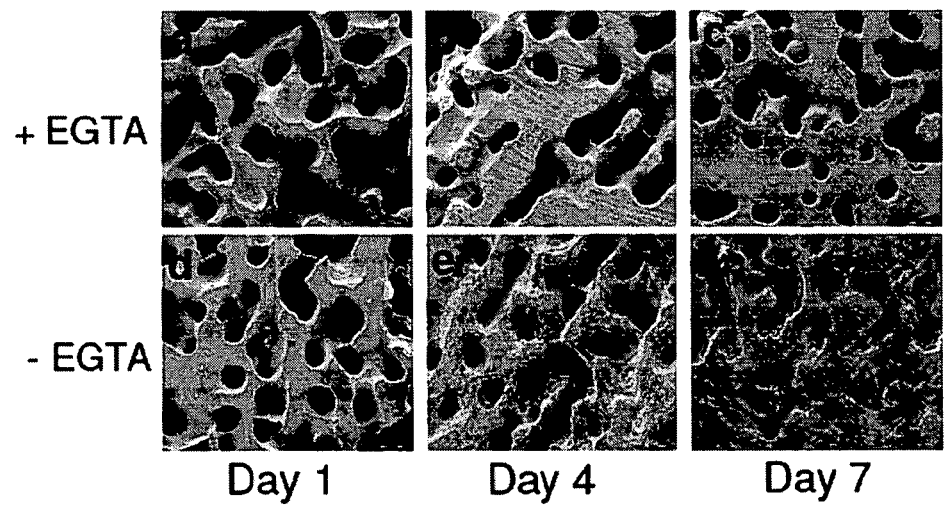

In one embodiment, coral is seeded with a precursor cell in culture in the presence of a chelator for a period of time sufficient to seed the precursor cell in the coral. In one embodiment, cells are cultured for up to 72 hours. In another embodiment, cells are cultured for up to 6 hours, 12 hours, 24 hours, 36 hours, 48 hours, 4 days, 5 days, 1 week, 1.5 weeks, 2 weeks, 3 weeks, or one month. In one embodiment, precursor enrichment occurs within 1 day of seeding (FIG. 2). In one embodiment, 50% of cells are seeded within 3 hours, 6 hours, 9 hours, 12 hours, 18 hours, 24 hours, 36 hours, 48 hours, 4 days, 5 days, or one week.

When such scaffolds are implanted at a site of bone and/or cartilage injury, bone and/or cartilage formation occurs. In one embodiment, such scaffolds lead to more rapid and increased quality bone and/or cartilage formation, lead to extensive remodeling, show evidence of integration and lead to new bone and/or cartilage with improved organization and strength.

In one embodiment, bone and/or cartilage formation in vivo and/or in vitro may be evaluated using one or more of the following markers. In one embodiment, since the functional hallmark of osteoblasts is their ability to mineralize the ECM, the incorporation of calcium into newly formed tissue (alizarin red staining) and the deposition of phosphate (von Kossa staining) as a measure of bone nodule formation may be followed. Possible fat accumulation, which would indicate differentiation of MSCs into adipocytes in the newly formed tissue, may also be monitored (oil red O staining). Differentiation of MSCs into osteoblasts may be evaluated in terms of alkaline phosphatase activity, an indicator of early osteoblast differentiation, and concentration of osteocalcin, which is secreted only by mature osteoblasts. Tissue formation may be evaluated in terms of concentrations of type I collagen, which is specific to bone, and DNA levels may be used as a measure of cell proliferation.

In addition, the methods of the present invention could be useful in the prevention and/or treatment of a variety of bone and/or cartilage-related disorders or injuries, as are known in the Art. In one embodiment of the invention, the mammal is a human in need of enhanced bone and/or cartilage formation. In one aspect, the human in need has a bone and/or cartilage deficit, which means that they will have less bone and/or cartilage than desirable or that the bone and/or cartilage will be less dense or strong than desired. A bone and/or cartilage deficit may be localized, such as that caused by a bone fracture or systemic, such as that caused by osteoporosis. Bone deficits may result from a bone remodeling disorder whereby the balance between bone formation and bone resorption is shifted, resulting in a bone deficit.

In one embodiment, the subject receiving the composition of the present invention has osteoporosis. In another embodiment, the subject has Paget's disease, fibrous dysplasias, or osteodystrophies. In another embodiment, the subject has bone and/or cartilage infirmity. In another embodiment, the subject has other bone remodeling disorders include osteomalacia, rickets, rheumatoid arthritis, achondroplasia, osteochodrytis, hyperparathyroidism, osteogenesis imperfecta, congenital hypophosphatasia, fribromatous lesions, multiple myeloma, abnormal bone turnover, osteolytic bone disease, periodontal disease, or a combination thereof. In one embodiment, bone remodeling disorders include metabolic bone diseases which are characterized by disturbances in the organic matrix, bone mineralization, bone remodeling, endocrine, nutritional and other factors which regulate skeletal and mineral homeostasis, or a combination thereof. Such disorders may be hereditary or acquired and in one embodiment, are systemic and affect the entire skeletal system.

Thus, in one aspect the human may have a bone remodeling disorder. Bone remodeling as used herein refers to the process whereby old bone is being removed and new bone is being formed by a continuous turnover of bone matrix and mineral that involves bone resorption by osteoclasts and bone formation by osteoblasts.

Osteoporosis is a common bone remodeling disorder characterized by a decrease in bone density of normally mineralized bone, resulting in thinning and increased porosity of bone cortices and trabeculae. The skeletal fragility caused by osteoporosis predisposes sufferers to bone pain and an increased incidence of fractures. Progressive bone loss in this condition may result in a loss of up to 50% of the initial skeletal mass.

Primary osteoporosis includes idiopathic osteoporosis which occurs in children or young adults with normal gonadal function, Type I osteoporosis, also described as post-menauposal osteoporosis, and Type II osteoporosis, senile osteoporosis, occurs mainly in those persons older than 70 years of age. Causes of secondary osteoporosis may be endocrine (e.g. glucocorticoid excess, hyperparathyroidism, hypoganodism), drug induced (e.g. corticosteroid, heparin, tobacco) and miscellaneous (e.g. chronic renal failure, hepatic disease and mal-absorption syndrome osteoporosis).

Those susceptible towards developing a bone and/or cartilage deficit may be beneficiaries of the methods of the present invention. In one embodiment, subjects susceptible to osteoporosis include post-menopausal women, elderly males (e.g. those over the age of 65), males on hormone-deprivation therapy for prostate cancer treatment or another reason, and those being treated with drugs known to cause osteoporosis as a side-effect (e.g. steroid-induced osteoporosis). Certain factors are well known in the art which may be used to identify those at risk of developing a bone and/or cartilage deficit due to bone and/or cartilage remodeling disorders such as osteoporosis. Important factors include low bone and/or cartilage mass, family history, life style, estrogen or androgen deficiency and negative calcium balance. Postmenopausal women are particularly at risk of developing osteoporosis.

The methods of the invention may also be used to enhance bone and/or cartilage formation in conditions where a bone and/or cartilage deficit is caused by factors other than bone remodeling disorders. Such bone deficits include fractures, bone trauma, conditions associated with post-traumatic bone surgery, post-prosthetic joint surgery, post plastic bone surgery, bone chemotherapy, post dental surgery and bone radiotherapy. Fractures include all types of microscopic and macroscopic fractures. In one embodiment, some examples of fractures includes avulsion fracture, comminuted fracture, transverse fracture, oblique fracture, spiral fracture, segmental fracture, displaced fracture, impacted fracture, greenstick fracture, torus fracture, fatigue fracture, intraarticular fracture (epiphyseal fracture), closed fracture (simple fracture), open fracture (compound fracture) and occult fracture. In one embodiment, fractures meant to be treated using the methods of the present invention are non-union fractures.

In one embodiment, this method may be used to: augment long bone fracture repair; generate bone in segmental defects; provide a bone graft substitute for fractures; facilitate tumor reconstruction or spine fusion; provide a local treatment (by injection) for weak or osteoporotic bone, such as in osteoporosis of the hip, vertebrae, or wrist, or a combination thereof. In another embodiment, the invention provides a method to accelerate the repair of fractured long bones; treat of delayed union or non-unions of long bone fractures or pseudoarthrosis of spine fusions; induce new bone formation in avascular necrosis of the hip or knee, or a combination thereof.

In one embodiment, the prosthetic or implant devices and other shaped products or structures of the present invention are provided for medical or related purposes. The term "medical or related purposes" is used throughout this specification to include the fields of human and non-human medicine and dentistry in particular. In one embodiment, a composition of the present invention may be used for restoration or replacement of both broken and diseased bone for orthopaedic, cranial, maxillofacial, dental and ocular and orbital floor implants. In another embodiment, a composition of the present invention may be used to replace lost bone trabeculae, which in one embodiment, may improve the mechanical strength of fixation for hip fractures.

In another embodiment, this invention provides a method of organ or tissue engineering in a subject, comprising the step of administering to a subject a composition comprising coral seeded with a precursor cell in culture in the presence of a chelator. In another embodiment, this invention provides a method of organ or tissue repair or regeneration in a subject, comprising the step of administering to a subject a composition comprising coral seeded with a precursor cell in culture in the presence of a chelator.

In one embodiment, the methods of this invention are useful in engineering, repairing or regenerating a connector tissue. The term "connector tissue" refers, in one embodiment to a tissue physically attached to two different tissues, providing a physical connection between them. In one embodiment, the connector tissue fulfills a non-specific connection, such as, for example, the presence of fascia. In another embodiment, the connector tissue confers functional properties, such as for example, tendons, ligament, articular cartilage, and others, where, in one embodiment, proper functioning of one or both tissues thereby connected is dependent upon the integrity, functionality, or combination thereof of the connector tissue.

For example, and in one embodiment, tendon attachment to bone, involves the insertion of collagen fibers (Sharpey's fibers) into the bone. The fibers have a distinct architecture, as compared to that of the collagen in the tendon, and in the bone. The mineral structure differs as well, in that tendons are free of hydroxyapatite, however, at regions, which are in closer proximity to the bone, the collagen fibers are calcified, by an increased hydroxyapatite crystal incorporation, and at regions of apposition to bone becomes essentially indistinguishable, in terms of its composition.

In one embodiment, use of the scaffolds for repair, regeneration of tissue is in cases where native tissue is damaged, in one embodiment, by trauma. In one embodiment, the coral of this invention is useful in repairing, regenerating or engineering the connector tissue, and in another embodiment, in facilitating the establishment of physical connections to the tissues, which connector tissue connects. For example, tendon repair, as well as its reattachment to bone may be facilitated via the use of the gradient scaffolds of this invention, and represents an embodiment thereof. In another embodiment, the gradient scaffold allows for incorporation of individual cells, which are desired to be present in the developing/repairing/regenerating tissue.

In one embodiment, the coral of the present invention may be used to adsorb or bind, and deliver, other therapeutically active substances which assist in the bone and/or cartilage repair or regeneration process, or which have other desired therapeutic activity. Such substances include, by way of example, known synthetic or semisynthetic antibiotics which may be introduced into the pore cavities of the shaped product or structure, or a growth factor such as transforming growth factor or one of the bone and/or cartilage morphogenic proteins which can be used to assist or promote bone and/or cartilage growth.

In any of the embodiments herein, coral for use in the present invention may further comprise, or be delivered with, other compounds such as, for example, antioxidants, growth factors, cytokines, antibiotics, anti-inflammatories, immunosuppressors, preservative, pain medication, other therapeutics, and excipient agents. In one embodiment, examples of growth factors that may be administered in addition to the HMG-CoA reductase inhibitor include, but are not limited to, epidermal growth factor (EGF), transforming growth factor-alpha (TGF-α), transforming growth factor-beta (TGF-β), human endothelial cell growth factor (ECGF), granulocyte macrophage colony stimulating factor (GM-CSF), bone morphogenetic protein (BMP), nerve growth factor (NGF), vascular endothelial growth factor (VEGF), fibroblast growth factor (FGF), insulin-like growth factor (IGF), cartilage derived morphogenetic protein (CDMP), platelet derived growth factor (PDGF), or any combinations thereof. Examples of antibiotics include antimicrobials and antibacterials.

In another embodiment, the present invention provides a kit, which in one embodiment, is a kit for bone and/or cartilage formation, and in one embodiment, comprises coral, precursor cells and a chelator. In one embodiment, the kit comprises coral, mesenchymal stem cells and a chelator. In another embodiment, the kit comprises coral, bone and/or cartilage precursor or stem cells, and a calcium chelator.

Any of the compositions described herein may be comprised in a kit. The kits will thus comprise, in suitable container means for the coral, precursor cells, chelators, or a combination thereof of the present invention, and any additional agents that can be used in accordance with the present invention. In one embodiment, any container of the kit will additionally comprise a preservative, which, in one embodiment, will increase the "shelf life" of the kit component or components to which it is added.

The kits may comprise suitably aliquoted compositions of the present invention. The components of the kits may be packaged either in aqueous media or in lyophilized form. The container means of the kits will generally include at least one vial, test tube, flask, bottle, syringe or other container means, into which a component may be placed, and suitably aliquoted. Where there is more than one component in the kit, the kit also will generally contain a second, third or other additional container into which the additional components may be separately placed. However, various combinations of components may be comprised in a vial.

The kits of the present invention also will typically include a means for containing reagent containers in close confinement for commercial sale. Such containers may include injection or blow-molded plastic containers into which the desired vials are retained.

When the components of the kit are provided in one and/or more liquid solutions, the liquid solution is an aqueous solution, which in one embodiment is a sterile aqueous solution. However, the components of the kit may be provided as dried powder(s). When reagents and/or components are provided as a dry powder, the powder can be reconstituted by the addition of a suitable solvent. In one embodiment, the solvent may also be provided in another container means.

Coral Coating

In one embodiment, the coral of the present invention has been substantially coated with a structural material, for example a metallic material such as silver, gold or titanium. In one embodiment a region or a plurality of sub-regions of the coral absent of plating material is provided, to allow bone and/or cartilage, adjacent thereto to make contact with and digest the coral. Conveniently, the coral can be coated with the metallic material by way of electroplating in one embodiment. When the coral becomes coated with the plating material, the metallic material penetrates the pores within the coral and becomes well anchored.

Electroplating is well known in the art and relates to the coating of an object with a thin layer of some metal through electrolytic deposition. The process is widely used, for the purpose of rendering a lustrous non-corrosive finish on some article. In electroplating, the general object is to employ the article to be plated as the cathode in an electrolytic bath composed of a solution of salt of the metal being plated. The other terminal, the anode may be made of the same metal, or it may be some chemically unaffected conductor. A low-voltage current is passed through the solution, which electrolyzes and plates the cathodic articles with the metal to the desired thickness.

In one embodiment, cell adhesion is a complex process that is important for maintaining tissue integrity and generating physical and permeability barriers within the body. Cell adhesion is mediated by specific cell surface adhesion molecules (CAMs). Among the many different families of CAMs, including the immununoglobulin, integrin, and selectin superfamilies, cadherins are a rapidly expanding family of calcium-dependent CAMs. The classical cadherins are integral membrane glycoproteins that generally promote cell adhesion through homophilic interactions (a cadherin on the surface of one cell binds to an identical cadherin on the surface of another cell), although cadherins also appear to be capable of forming heterotypic complexes with one another under certain circumstances and with lower affinity. Cadherins have been shown to regulate epithelial, endothelial, neural and cancer cell adhesion, with different cadherins expressed on different cell types. N (neural)—cadherin is predominantly expressed by neural cells, endothelial cells and a variety of cancer cell types. E (epithelial)—cadherin is predominantly expressed by epithelial cells. Other cadherins are P (placental)—cadherin, which is found in human skin and R (retinal)—cadherin.

Figure 4:
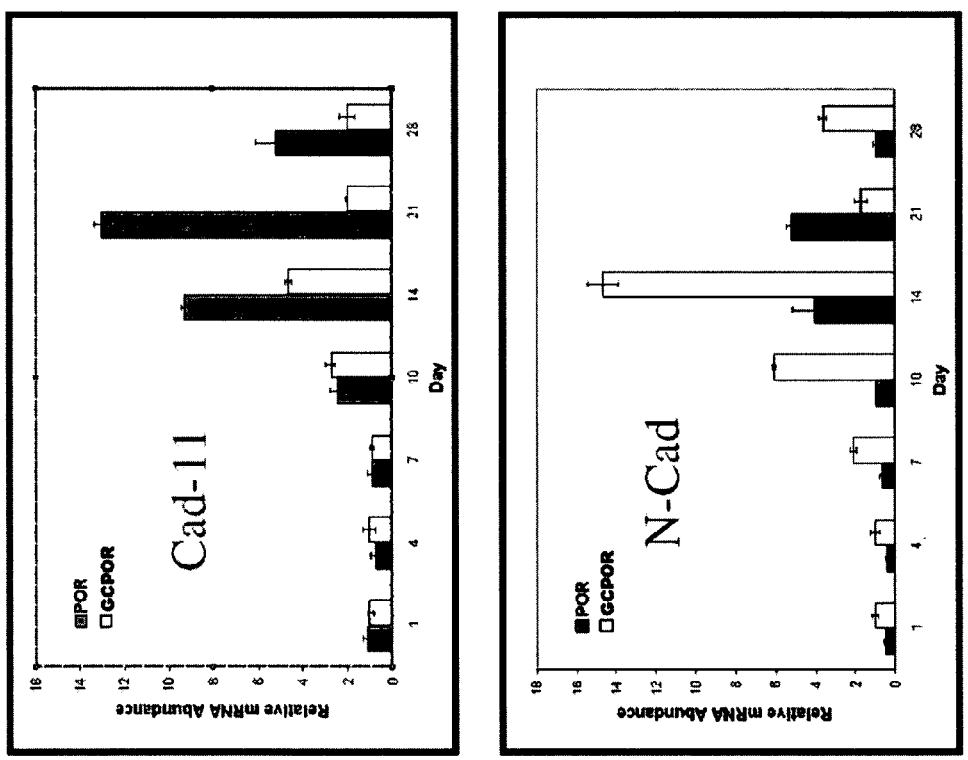
FIG. 4 presents cadherin mRNA expression in MSCs seeded on porites lutea (POR). (A) mRNA expression of cadherin-11 (Cad-11) in MSCs seeded on POR and gold-coated POR (GOLD) biomatrices on different days post seeding. The mRNA expression levels are shown as fold changes±SD, relative to the expression level of GOLD biomatrices on day 1. (B) mRNA expression of N-cadherin (N-Cad) in MSCs seeded on porites lutea (POR) and gold-coated POR (GOLD) biomatrices on different days post seeding. The mRNA expression levels are shown as fold changes±SD, relative to the expression level of GOLD biomatrices on day 1.

This invention is further directed to use of cadherin-up-regulating coral for treating cancer or inhibiting cancer progression. Surprisingly, growth of mesenchymal stem cells on Porites Lutea upregulated cadherin mRNA (Example 3, FIG. 4).

Without being bound by theory, Applicants propose that, in one embodiment, contact of MSCs with the $CaCO_3$ biomatrix leads to high calcium concentration and calcium uptake that may in turn affect the stabilization of the extracellular domain of cadherin molecules and/or stimulate their expression through calcium signaling. β-catenin can be found in three cellular locations: bound to the cadherin molecules, in the cytoplasm, interacting with the APC, GSK and axin complex, or in the nucleus, acting as a coactivator for LEF/TCF. Normally, β-catenin is phosphorylated by GSK, ubiquitinized, and targeted for degradation. When Wnt ligand binds to its receptor; it activates Dsh, which in turn inactivates GSK. β-catenin accumulates in the cytoplasm, enters the nucleus and interacts with the transcription factors to activate the expression of target genes. Thus, stabilization and/or expression of cadherins can modulate β-catenin signaling (based on Rowlands, 2005).

Cadherin function and/or expression have been implicated in cancer progression and metastasis. Downregulation of certain cadherins decreases the strength of cellular adhesion within a tissue, resulting in an increase in cellular motility, allowing cancer cells to cross the basement membrane and invade surrounding tissues.

In early neoplasia, cadherins play a role in the transformation of cells to an abnormal proliferative phenotype. Some cadherins are involved in inducing cell cycle arrest. However, some cadherins also promote cell survival in normal cancerous cells. In some cases, one type of cadherin is downregulated accompanied by the upregulation of other cadherins.

Thus, in one embodiment, the present invention provides a method of treating cancer or inhibiting cancer progression comprising contacting a neoplastic, pre-neoplastic, or hyperplastic cell in a subject with a composition comprising coral, wherein said coral upregulates cadherin levels and wherein said coral is from the *Porites* or *Acropora* species.

In another embodiment, the present invention provides a method of preventing a relapse to cancer, reducing the incidence of cancer, prolonging the remission of cancer, or treating a precancerous precursor comprising contacting a neoplastic, pre-neoplastic, or hyperplastic cell in a subject with a composition comprising coral, wherein said coral upregulates cadherin levels.

In one embodiment, a neoplastic cell is a tumor cell, and may be present in tumors, or tissue or body fluids containing tumor cells. In one embodiment, neoplastic refers to abnormal, disorganized growth in a tissue or organ, usually forming a distinct mass. In one embodiment, such a growth is called a neoplasm, also known as a tumor. In another embodiment, neoplastic means cancerous. In one embodiment, neoplastic cells may be benign or malignant. In one embodiment, a pre-neoplastic cell is a cell that is morphologically identifiable as having a high malignant potential, but is not considered neoplastic.

In one embodiment, hyperplastic refers to a cell within an organ or tissue that shows an increase in size due to an increased number of cells. In one embodiment, hyperplasia may be due to increased demand, chronic inflammatory response, hormonal dysfunctions, neoplasia, or a combination thereof.

In one embodiment, "treating" refers to both therapeutic treatment and prophylactic or preventative measures, wherein the object is to prevent or lessen the targeted pathologic condition or disorder as described hereinabove. Thus, in one embodiment, treating may include directly affecting or curing, suppressing, inhibiting, preventing, reducing the severity of, delaying the onset of, reducing symptoms associated with the disease, disorder or condition, or a combination thereof. Thus, in one embodiment, "treating" refers inter alia to delaying or inhibiting progression, expediting remission, inducing remission, augmenting remission, speeding recovery, increasing efficacy of or decreasing resistance to alternative therapeutics, or a combination thereof. In one embodiment, "preventing" refers, inter alia, to delaying the onset of symptoms, reducing the incidence of the disease, prolonging the remission of a disease, or treating a precursor of a disease, or a combination thereof. In another embodiment, preventing refers to preventing relapse to a disease, decreasing the number or frequency of relapse episodes, increasing latency between symptomatic episodes, or a combination thereof. In one embodiment, "suppressing" or "inhibiting", refers inter alia to reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

In one embodiment, symptoms are primary, while in another embodiment, symptoms are secondary. In one embodiment, "primary" refers to a symptom that is a direct result of a disease or disorder, while in one embodiment, "secondary" refers to a symptom that is derived from or consequent to a primary cause. In one embodiment, the compositions for use in the present invention treat primary or secondary symptoms or secondary complications.

In another embodiment, "symptoms" may be any manifestation of a disease or pathological condition, comprising inflammation, swelling, fever, pain, bleeding, itching, runny nose, coughing, headache, migraine, dizziness, blurry vision, etc., or a combination thereof. In one embodiment, symptoms comprise itchy eyes, swollen eyelids, redness, irritation, watery eyes, mucoid discharge, pain, or a combination thereof.

In one embodiment, the methods of the present invention treat cancer, which in one embodiment, manifests as a tumor. In one embodiment, the tumor is a laryngeal, colon, rectal, prostate, breast, thoracic, bladder or skin tumor. In another embodiment, the tumor is a thoracic tumor such as, but not limited to, bronchogenic tumors, such as primary and/or metastatic lung carcinomas [both non-small cell lung cancer (NSCLC) and small cell lung cancer (SCLC)]; malignant pleural effusions; or cancers of the lung parenchyma, airways, chest wall and pleural spaces. In another embodiment, the tumor is a lung solid tumor; laryngeal tumor, brain tumor, or other tumor of the head and neck; colon, rectal or prostate tumor; breast or thoracic solid tumor; ovarian or uterine tumor; tumor of the esophagus, stomach, pancreas or liver; bladder or gall bladder tumor; skin tumor such as melanoma; and the like, or a combination thereof. Moreover, the tumor treated in the invention can be either primary or a secondary tumor resulting from metastasis of cancer cells elsewhere in the body.

For the purposes of the invention, compositions of the invention are contacted with cells, which in one embodiment are neoplastic, pre-neoplastic, or hyperplastic cells. In another embodiment, cells may be cytologically dysplastic and/or premalignant. "Hyperplastic cells" include, in one embodiment, normal cells in a normal arrangement in a tissue, which exhibit abnormal multiplication or increase in cell numbers, for example, as is common in benign prostatic hyperplasia. Cytologically dysplastic and/or premalignant cellular growth or proliferation includes increases in cellular numbers of karyotypically abnormal but non-malignant cells within a tissue. Examples include some benign prostatic hyperplasias/dysplasia and cervical hyperplasias/dysplasias.

"Neoplastic cells", in one embodiment, are cells displaying abnormally organized tissue, includes malignant and non-malignant neoplasms. Malignant neoplasms include primary, recurrent, and/or or metastatic cancerous tumors originating in any tissues, for example, carcinomas, sarcomas, lymphomas, mesotheliomas, melanomas, gliomas, nephroblastomas, glioblastomas, oligodendrogliomas, astrocytomas, ependymomas, primitive neuroectodermal tumors, atypical meningiomas, malignant meningiomas, or neuroblastomas, originating in the pituitary, hypothalamus, lung, kidney, adrenal, ureter, bladder, urethra, breast, prostate, testis, skull, brain, spine, thorax, peritoneum, ovary, uterus, stomach, liver, bowel, colon, rectum, bone, lymphatic system, skin, or in any other organ or tissue of the subject.

Dosages and Routes of Administration

The present invention encompasses use of compositions as described herein for treating cancer, inhibiting cancer progression, preventing relapse to cancer, reducing the incidence of cancer, prolonging the remission of cancer, or treating a precancerous precursor.

In one embodiment, compositions of this invention are pharmaceutically acceptable. In one embodiment, the term "pharmaceutically acceptable" refers to any formulation which is safe, and provides the appropriate delivery for the desired route of administration of an effective amount of at least one compound for use in the present invention. This term refers to the use of buffered formulations as well, wherein the pH is maintained at a particular desired value, ranging from pH 4.0 to pH 9.0, in accordance with the stability of the compounds and route of administration.

In one embodiment, coral of this invention may be administered alone or within a composition. In another embodiment, compositions comprising coral in admixture with conventional excipients, i.e. pharmaceutically acceptable organic or inorganic carrier substances suitable for parenteral, enteral (e.g., oral) or topical application which do not deleteriously react with the active compounds may be used. In one embodiment, suitable pharmaceutically acceptable carriers include but are not limited to water, salt solutions, alcohols, gum arabic, vegetable oils, benzyl alcohols, polyethylene glycols, gelatine, carbohydrates such as lactose, amylose or starch, magnesium stearate, talc, silicic acid, viscous paraffin, white paraffin, glycerol, alginates, hyaluronic acid, collagen, perfume oil, fatty acid monoglycerides and diglycerides, pentaerythritol fatty acid esters, hydroxy methylcellulose, polyvinyl pyrrolidone, etc. In another embodiment, the pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. In another embodiment, they can also be combined where desired with other active agents, e.g., vitamins.

In one embodiment, the therapeutic compositions of the instant invention comprise coral and additional compounds effective in preventing or treating cancer or cancer-related disorders. In one embodiment, the additional compounds comprise anti-inflammatory compositions, which in one embodiment are non-steroidal anti-inflammatory medications, antihistamines, antibiotics, corticosteroids, cromolyn sodium (sodium cromoglicate), mast-cell stabilizers, or a combination thereof.

In one embodiment such additional compounds may be anti-cancer drugs, which in one embodiment, may inhibit nucleotide formation and may inter alia include drugs such as alia methotrexate (Abitrexate®), fluorouracil (Adrucil®), hydroxyurea (Hydrea®), mercaptopurine (Purinethol®), or a combination thereof. In another embodiment, such anti-cancer drugs may damage DNA and may inter alia include drugs such as cisplatin (Platinol®) and 7) antibiotics—daunorubicin (Cerubidine), doxorubicin (Adriamycin®), etoposide (VePesid®), or a combination thereof. In another embodiment, such anti-cancer drugs may be alkylating agents such as Nitrogen Mustard or Cyclosporamide. In another embodiment, such anti-cancer drugs may affect the synthesis or breakdown of the mitotic spindles and may inter alia include drugs such as Vinblastine (Velban®), Vincristine (Oncovin®), Pacitaxel (Taxol®), or a combination thereof.

In one embodiment, the therapeutic compositions of the instant invention are administered with other treatments that relieve symptoms.

In one embodiment, the route of administration may be parenteral, enteral, or a combination thereof. In another embodiment, the route may be intratumoral, parcanceral, topical, intraperitoneal, intravenous, intra-arterial, transdermal, intradermal, subcutaneous, vaginal, rectal, transmucosal, intramuscular, intravascular, intraventricular, intracranial, inhalation, nasal aspiration (spray), sublingual, oral, intra-ocular, conjunctival, aerosol or suppository or a combination thereof.

In one embodiment, the dosage regimen will be determined by skilled clinicians, based on factors such as exact nature of the condition being treated, the severity of the condition, the age and general physical condition of the patient, etc.

In one embodiment, "intratumoral" administration means implanting a reservoir of a therapeutic agent(s) inside a tumor. Intratumoral administrations is advantageous for tumor treatment because the outer cell layers of tumors are often composed of a high percentage of necrotic cells and/or connective and support tissue which slow and/or impede the extra-tumoral vascular or parenteral delivery of therapeutic agents to the actively growing cancer cells at the center of solid tumors.

For parenteral application, particularly suitable are injectable, sterile solutions, in one embodiment, oily or aqueous solutions, as well as suspensions, emulsions, or implants, including suppositories and enemas. Ampoules are convenient unit dosages. Such a suppository may comprise any agent described herein.

For application by inhalation, solutions or suspensions of the compounds mixed and aerosolized or nebulized in the presence of the appropriate carrier suitable. Such an aerosol may comprise any agent described herein.

For topical application, particularly in the area around the eye, an admixture of the compounds with conventional creams, lotions, or delayed release patches is acceptable. Such a cream or lotion may comprise any agent described herein.

For enteral application, particularly suitable are tablets, dragees, liquids, drops, or capsules. A syrup, elixir, or the like can be used when a sweetened vehicle is employed.

For intra-ocular application, eye drops, ointments, lotions, creams, or coated eye patches may be used in one embodiment.

Sustained or directed release compositions can be formulated, e.g., liposomes or those wherein the active compound is protected with differentially degradable coatings, e.g., by microencapsulation, multiple coatings, etc. It is also possible to freeze-dry the new compounds and use the lyophilisates obtained, for example, for the preparation of products for injection. In one embodiment, the composition of the present invention may be an extended release composition. In one embodiment, the expression "extended release", as used herein, includes, without limitation various forms of release, such as controlled release, timed release, sustained release, delayed release, long acting, and pulsatile delivery, immediate release that occurs with various rates. The ability to obtain extended release, controlled release, timed release, sustained release, delayed release, long acting, pulsatile delivery or immediate release is performed using well-known procedures and techniques available to the ordinarily skilled artisan.

Thus, in one embodiment, the route of administration may be directed to an organ or system that is directly affected by cancer. For example, coral may be administered in intratumorally. In another embodiment, the route of administration may be directed to a different organ or system than the one that is affected by the disease. For example, compounds may be administered to a distal site or to a site downstream of the tumor to treat a tumor. Thus, the present invention provides for the use of coral of the present invention in various dosage forms suitable for administration using any of the routes listed hereinabove.

In one embodiment, the doses of coral in ground or powdered form utilized for any of the above-described purposes will generally be administered at a dose of from 1 to about 1000 milligrams per kilogram of body weight (mg/kg), administered one to four times per day, or by continuous IV infusion. When the compositions are dosed topically or intraocularly, they will generally be in a concentration range of from 0.1 to about 10% w/v, administered 1, 2, 3, or 4 times per day. In another embodiment, 0.5 to 5%, and in another embodiment, 1-4%.

In one embodiment of the invention, the concentrations of the compositions will depend on various factors, including the nature of the condition to be treated, the condition of the patient, the route of administration and the individual tolerability of the compositions.

It will be appreciated that the actual preferred amounts of active composition in a specific case will vary according to the particular compositions formulated, the mode of application, and the particular conditions and organism being treated. Dosages for a given host can be determined using conventional considerations, e.g., by customary comparison of the differential activities of the subject compounds and of a known agent, e.g., by means of an appropriate, conventional pharmacological protocol.

In one embodiment, the compositions of the invention may be administered acutely for acute treatment of temporary conditions, or may be administered chronically, especially in the case of progressive, recurrent, or degenerative disease. In one embodiment, one or more compounds of the invention may be administered simultaneously, or in another embodiment, they may be administered in a staggered fashion. In one embodiment, the staggered fashion may be dictated by the stage or phase of the disease.

In one embodiment, a solid article comprising the composition of the invention is inserted into the solid tumor being treated by implantation, injection, or otherwise being placed within the tumor of the subject being treated, for example, during or after the surgical removal of a portion of visibly cancerous tissue.

In another embodiment, compositions for use in accordance with the present invention are given in non-solid form. In one embodiment, the compositions are produced according to a process comprising washing naturally occurring coral sand with water to desalinate it, then disinfecting and drying the desalinated coral sand at temperatures of about 80° to about 150° C., preferably 90° to 120° C., and grinding the disinfected and dried coral into small particles, which in one embodiment comprise particles of 1-10 microns. In another embodiment, coral is ground into particles of 1-5,1-20, 1-50, 1-100, 5-10, 10-15, 15-20, 10-50, 10-100, 20-100, or 50-100 microns. In another embodiment, coral is ground to 150 to about 500 mesh. The grinding can also be effected either by freeze drying the disinfected and dried coral sand at temperatures of about −180° C. to −200° C. in a nitrogen atmosphere, or in a state where coral sand has been kneaded together with seawater or fountain water.

The thus obtained finely divided coral sand powders are extremely finely porous and have high solubility in water. The so obtained coral sand powders may be dissolved in water (the powders dissolve in the form of ions) as they are and the resulting solution can be provided as drinking water. Alternatively, the fine powders of the coral sand may be formulated as granules, tablets, emulsions, pills, suspension concentrates, etc., in the presence or absence of binders. Granules are usually manufactured by agglomeration or impregnation techniques. Generally granules will contain 0.5 to 25% by weight of the coral sand fine powders and 0 to 10% by weight of additives, if necessary and desired, such as stabilizers, slow release modifiers and binders. Tablets or pills may be manufactured in conventional manners, by mixing with binders such as starch, gelatin, etc. and the tableting the mixture using a tableting machine.

The composition of the present invention may also contain other ingredients, for example, various nutrients such as vitamins (vitamins A, B, C, E, F, etc.), sugars (glucose, fructose, sucrose, maltose, or the like), etc. Further, the coral sand powders per se may also be employed as additives to various foodstuffs.

In one embodiment, the composition is administered to adults at a daily dose of 1.0 to 10 g.

In another embodiment, the present invention provides a method of in vivo calcium release comprising contacting cells in a subject with an aragonite or calcite-producing species, whereby cells recruited to said aragonite or calcite promote calcium release from said aragonite or calcite.

This invention provides, in some embodiments, methods and compositions for enhanced localized calcium release, which in turn may recruit stem and/or progenitor cells to the site, stimulate tissue regeneration or repair, in multiple tissue types.

Calcium is an important factor for appropriate skin health. The calcium integrity of the upper epidermis is known to regulate major skin functions. Calcium regulates cell turnover [via cell "differentiation" stimulated by the protein kinase C (PKC) enzyme. Increased epidermal calcium stimulates rapid cell turnover and, therefore, turnover can be up-regulated with absorbable topical calcium resulting in plumper looking skin.

Calcium regulates the lipid barrier process. Peeling, microdermabrasion and cold winter weather strip the skin's moisture barrier. A high calcium content in the upper epidermis helps maintain continual and efficient barrier functions. Subjects with dry skin or dry skin due to weather respond well to topical calcium treatment. Calcium can significantly reduce dryness caused by microdermabrasion making the skin look well hydrated and fuller in appearance.

Epidemiologic studies have shown that low skin calcium content results in premature aging of the skin and a greater incidence of skin cancer while conversely, people with high skin calcium content experience less premature skin aging and less incidence of skin cancer. Calcium may also serve as a regulator of the skin's production of antioxidants, for example via promotion of catalase activity.

Antioxidants prevent DNA damage leading to premature aging of the skin and skin cancer, in part by preventing damage to collagen and elastin and other skin components. Application of the compounds/compositions of this invention, for example, topical or dermal injectable delivery may enhance localized calcium concentrations, and in some embodiments, thus inhibits the aging of the skin via its up-regulation of antioxidants.

Injectable dermal fillers are used extensively for the augmentation of soft tissue, such as for removing wrinkles, treating dermal scarring due to trauma, acne, surgery and the like, or for augmenting soft tissue of the lips and nasolabial folds. Such fillers are well known in the art, see for example, WO06102676A1. In some embodiments, the coral compositions of this invention will be formulated as an injectable dermal filler. In some embodiments, the coral will conform to any embodiment as described herein, including for example, powdered forms. In some embodiments, the composition will further comprise a chelator, as herein described. In some embodiments, the chelator will be formulated to be released after application to a skin surface in the subject, by means known in the art.

The injectable composition may, in addition to including the corals as described herein, and optionally a chelator as described herein, further comprise crosslinked hyaluronic acid, e.g., bodies or particulates consisting essentially of hyaluronic acid having a particle size and configuration that are injectable by an injector, such as injectable through a needle. In some embodiments, injectable compositions of this invention may comprise particles of a size and configuration such that they are injectable through a syringe needle ranging in size from 18 to 33 gauge, or in some embodiments, 24 to 31 gauge, or in some embodiments, 27 to 30 gauge.

In some embodiments, such compositions for skin application may also comprise zinc, betaglucan and panthenol to promote healing.

In some embodiments, any of the compositions of this invention will comprise a coral, in any form or embodiment as described herein. In some embodiments, any of the compositions of this invention will consist of a coral, in any form or embodiment as described herein. In some embodiments, of the compositions of this invention will consist essentially of a coral, in any form or embodiment as described herein. In some embodiments, the term "comprise" refers to the inclusion of the indicated active agent, such as the coral, or the coral and chelator, as well as inclusion of other active agents, and pharmaceutically acceptable carriers, excipients, emollients, stabilizers, etc., as are known in the pharmaceutical industry. In some embodiments, the term "consisting essentially of" refers to a composition, whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" may refer to components which facilitate the release of the active ingredient. In some embodiments, the term "consisting" refers to a composition, which contains the active ingredient and a pharmaceutically acceptable carrier or excipient.

In some embodiments, the compositions of this invention are for cosmetic purposes, and may comprise a powder, a cream, a foam, a makeup, an oil, a scrub, or any cosmetic composition as known in the art.

In some embodiments, the compositions will comprise a coral, and optionally a chelator as described herein, and other active agents suitable for use in the compositions of the invention, including in some embodiments, cosmetic active agents intended to improve the aesthetic appearance of the skin and/or lips.

In some embodiments, the composition according to the invention can additionally comprise at least one agent chosen from:—agents which act on the microcirculation,—desquamating and moisturizing agents,—depigmenting or propigmenting agents,—antiglycation agents,—agents which stimulate the synthesis of dermal or epidermal macromolecules and/or which prevent their decomposition,—agents which stimulate the proliferation of fibroblasts or keratinocytes and/or the differentiation of keratinocytes,—muscle relaxants or dermo-decontracting agents,—tightening agents,—agents for combating pollution or free radicals,—soothing agents.

Agents which act on the microcirculation The active agents which act on the micro-circulation (vasoprotective or vasodilatory agents) can be chosen from flavonoids, ruscogenins, esculosides, the aescin extracted from horse chestnut, nicotinates, hesperidin methyl chalcone, essential oils of lavender or rosemary, or *Ammi visnaga* extracts.

Mention may also be made of (β-hydroxy-ethyl)rutoside or trimethylrutoside; *Arnica* extracts; nicotinic acid and its derivatives, such as nicotinic acid esters, for example xanthinol nicotinate or inositol nicotinate; salicylic acid and its esters; dihydroergotoxine methanesulphonate, dihydroergocornine methanesulphonate, dihydroergocristine methanesuiphonate, cinnarizine, vincamine, pentoxifylline, bamethan sulphate, bencyclane hydrogen fumarate, 3-pyridylcarbinol, Ginkgo flavoglycosides, Calendulae extracts, hesperidin, a-G-hesperidin, and their mixtures. Mention may also be made of visnadin or esculoside, amentoflavone or Ginko biloba dimers in the free form or complexed with phospholipids, icarin and derivatives or extracts comprising them, aescin, aescin 13-sitosterol complexed with phospholipids, sericoside, optionally complexed with phospholipids, or a *Centella asiatica* extract in the free form or complexed with phospholipids, such as disclosed in Application Desguamating and moisturizing agents The term "desquamating agent" is understood to mean any compound capable of acting:—either directly on desquamation by promoting exfoliation, such as J3-hydroxy acids, in particular salicylic acid and its derivatives (including S-(n-octanoyl) sal±cylic acid); a-hydroxy acids, such as glycolic acid, citric acid, lactic acid, tartaric acid, malic acid or mandelic acid; urea; gentisic acid; oligofucoses; cinnamic acid; *Saphora japonica* extract; resveratrol and some jasmonic acid derivatives;—or on the enzymes involved in desquamation or decomposition of the comeodesmosomes, such as glycosidases, stratum corneum chymotryptic enzyme (SCCE) or indeed even other proteases (trypsin, chymotrypsin-Wile). Mention may be made of agents which chelate inorganic salts: EDTA; N-acyl—N,N',N'-etl-iylene_diaminetriacetic acid; aminosulphonic compounds and in particular N-(2-hydroxyethyl)p±perazjne_N'-2-ethane-sulphonic acid (HEPES); 2-oxothiazolid±ne-4-carboxyljc acid (procysteine) derivatives; derivatives of a-amino acids of glycine type (as disclosed in EP-0 852 949, and also the sodium methylglycinediacetate sold by BASE' under the trade name Trilon M); honey; or sugar derivatives, such as O-octanoyl-6-D-maltose and N-acetylglucosamine.

The term "moisturizing agent" is understood to mean:— either a compound which acts on the barrier function, for the purpose of keeping the stratum corneum moisturized, or an occlusive compound. Mention may be made of ceramides, sphingoid-based compounds, lecithins, glycosphingolipids, phospholipids, cholesterol and its derivatives, phytosterols (stigmasterol, 3-sitosterol or campesterol), essential fatty acids, 1,2-diacyiglycerol, 4-chromanone, pentacyclic triterpenes, such as ursolic acid, petroleum jelly and lanolin;—or a compound which directly increases the water content of the stratum corneum, such as threalose and its derivatives, hyaluronic acid and its derivatives, glycerol, pentanediol, sodium pidolate, serine, xylitol, sodium lactate, glyceryl polyacrylate, ectoin and its derivatives, chitosan, oligo- and polysaccharides, cyclic carbonates, N-lauroylpyrrolidonecarboxylic acid and N-a-benzoyl-L-arginine;—or a compound which activates the sebaceous glands, such as steroid derivatives (including DHEA or its 7-oxidized and/or 17-alkylated derivatives, and sapogenins), methyl dihydrojasmonate, and vitamin D and its derivatives.

These compounds may in some embodiments, represent from 0.001% to 30% or in other embodiments, from 0.01 to 20% of the total weight of the composition according to the invention.

Pigmenting or propigmenting agents—The depigmenting or antipigmenting agents capable of being incorporated in the composition according to the present invention comprise, for example, the following compounds: kojic acid; ellagic acid; arbutin and its derivatives, such as those disclosed in Applications EP-895 779 and EP-524 109; hydroquinone; aminophenol derivatives, such as those disclosed In Applications WO 99/10318 and WO 99/32077, in particular N-cholesteryloxycarbonyl-para-aminophenol and N-ethyloxycarbonyl-para-aminophenol; iminophenol derivatives, in particular those disclosed in Application WO 99/22707; L-2-oxothiazolidine-4-carboxylic acid or procysteine, and its salts and esters; calcium D-pantetheinesulphonate; ascorbic acid and its derivatives, in particular ascorbyl glucoside; and plant extracts, in particular of liquorice, of blackberry, of skull cap and of *Bacopa monnieri*, without this list being limiting.

Mention may be made, as propigmenting agent, of the extract of burnet (*Sanguisorba officinalis*) sold by *Maruzen* and extracts of chrysanthemum (*Chrysanthemum morifolium*) Antiglycation agents The term "antiglycation agent" is understood to mean a compound which prevents and/or reduces the glycation of skin proteins, in particular of dermal proteins, such as collagen.

Examples of antiglycation agents are plant extracts of the Ericaceae family, such as an extract of blueberry (*Vaccinium angustifolium*); ergothioneine and its derivatives; and hydroxystilbenes and their derivatives, such as resveratrol and 3,3',5,5'-tetrahydroxystilbene. These antiglycation agents are disclosed in Applications FR 2 802 425, FR 2 810 548, FR 2 796 278 and FR 2 802 420, respectively.

Resveratrol is used in some embodiments of the compositions of this invention.

Agents which stimulate the synthesis of dermal or epidermal macromolecules and/or which prevent their decomposition. Mention may be made, among the active agents which stimulate dermal macromolecules or which prevent their decomposition, of those which act:—either on the synthesis of collagen, such as extracts of Centella asiatica; asiaticosides and derivatives; ascorbic acid or vitamin C and its derivatives; synthetic peptides, such as iamine, biopeptide CL or the palmitoyloligopeptide sold by Sederma; peptides extracted from plants, such as the soybean hydrolysate sold by Coletica under the trade name Phytokine®; and plant hormones, such as auxins and lignans;—or on the synthesis of elastin, such as the extract of *Saccharomyces cerevisiae* sold by LSN under the trade name Cytovitin®; and the extract of the alga *Macrocystis pyrifera* sold by Secma under the trade name Kelpadelie®;—or on the synthesis of glycosaminoglycans, such as the product of fermentation of milk by *Lactobacillus vulgaris* sold by Brooks under the trade name Biomin Yogourth®; the extract of the brown alga *Padina pavonica* sold by Alban Muller under the trade name HSP3®; and the extract of *Saccharomyces cerevisiae* available in particular from Silab under the trade name F.irmalift® or from LSN under the trade name Cytovitin®;—or on the synthesis of fibronectin, such as the extract of Sauna zooplankton sold by Seporga under the trade name GP4G®; the yeast extract available in particular from Alban Muller under the trade name Drieline®; and the palmitoyl pentapeptide sold by Sederma under the trade name Matrixil®;—or on the inhibition of metalloproteinases (MMP), such as more particularly MMP 1, 2, 3 or 9. Mention may be made of: retinoids and derivatives; oligopeptides and lipopeptides; lipoamino acids; the malt extract sold by Coletica under the trade name Collalift®; extracts of blueberry or of rosemary; lycopene; or isoflavones, their derivatives or the plant extracts comprising them, in particular extracts of soybean (sold, for example, by Ichimaru Pharcos under the trade name Flavosterone SBS), of red clover, of flax, of kakkon or of sage;—or on the inhibition of serine proteases, such as leukocyte elastase or cathepsin G. Mention may be made of: the peptide extract of Leguminosae (*Pisum sativura*) seeds sold by LSN under the trade name Parelastyl®; heparinoids; and pseudodipeptides, such as {2-[acetyl (3-(trifluoromethyl) phenyl) amino] -3-methyl-butyrylamino}acetic acid.

Mention may in particular be made, among the active agents which stimulate epidermal macromolecules, such as filaggrin and keratins, of the extract of lupin sold by Silab under the trade name Structurine®; the extract of beech *Fagus sylvatica* buds sold by Gattefoss' under the trade name Gatuline®; and the extract of Salina zooplankton sold by Seporga under the trade name GP4G®.

Agents which stimulate the proliferation of fibroblasts or keratinocytes and/or the differentiation of keratinocytes The agents which stimulate the proliferation of fibroblasts which can be used in the composition according to the invention can, for example, be chosen from plant proteins or polypeptides, extracts, in particular of soybean (for example, a soybean extract sold by LSN under the name Eleseryl SH-VEG 8® or sold by Silab under the trade name Raffermine®); and plant hormones, such as gibberellins and cytokinins.

The agents which stimulate the proliferation of keratinocytes which can be used in the composition according to the invention comprise in particular retinoids, such as retinol and its esters, including retinyl palmitate; adenosine; phloroglucinol; the extracts of walnut meal sold by Gattefoss; and the extracts of *Solanura tuberosum* sold by Sederma.

The agents which stimulate the differentiation of keratinocytes comprise, for example, inorganic materials, such as calcium; a peptide extract of lupin, such as that sold by Silab under the trade name Structurine®; sodium 3-s±tosteryl sulphate, such as that sold by Seporga under the trade name Phytocohesine®; and a water-soluble extract of maize, such as that sold by Solabia under the trade name Phytovityl®; a peptide extract of Voandzeia subterranea, such as that sold by Laboratoires Srobiologiques under the trade name Filladyn LS 9397®; and lignans, such as secoisolariciresinol.

Muscle relaxants or dermo-decontracting agents The muscle relaxants or dermo-decontracting agents which can be used in the composition according to the invention comprise alverine and its salts, manganese gluconate, diazepam, the hexapeptide Argireline R sold by Lipotec, some carbonylated secondary and tertiary amines, adenosine, and also sapogenins and the natural extracts, in particular of wild yam, comprising them, and also *Boswellia serrata* extracts.

Tightening agents The term "tightening agent" is understood to mean a compound capable of exerting tension on the skin, the effect of which is to temporarily render less distinct unevennesses in the surface of the skin, such as wrinkles and fine lines.

Mention may in particular be made, among the tightening agents which can be used in the composition according to the present invention, of: (1) synthetic polymers, such as polyurethane latices or acrylic-silicone latices, in particular those disclosed in Patent Application EP-1 038 519, such as a polydimethylsiloxane grafted with propylthio [ poly (methyl acrylate) 3, propylthio [poly-(methyl methacrylate) ] and propylthio[poly(methacrylic acid)] or a polydimethylsiloxane grafted with propylthio [poly (isobutyl methacrylate)] and propylthio[poly(methacrylic acid)]. Such grafted silicone polymers are sold in particular by 3M under the trade names VS 80, VS 70 or L021, (2) polymers of natural origin, in particular (a) polysaccharides, for example (i) in the form of starch resulting in particular from rice, maize, potato, manioc, peas, wheat, oats, and the like, or (ii) in the form of carrageenans, alginates, agars, gellans, cellulose polymers and pectins, advantageously as an aqueous dispersion of gel microparticles, and (b) latices composed of shellac resin, gum sandarac, dammars, elemis, copals, cellulose derivatives, and their mixtures, (3) plant proteins and protein hydrolysates, in particular of maize, rye, wheat, buckwheat, sesame, spelt, peas, broad beans, lentils, soybeans and lupin, (4) mixed silicates, in particular phyllosilicates and especially laponites, (5) wax microparticles, for example chosen from carnauba, candelilla or lucerne waxes, (6) colloidal particles of inorganic filler having a number-average diameter of between 0.1 and 100 nm, preferably between 3 and 30 nm, and chosen, for example, from: silica, silica/alumina composites, cerium oxide, zirconium oxide, alumina, calcium carbonate, barium sulphate, calcium sulphate, zinc oxide and titanium dioxide.

Agents for combating pollution or free radicals The expression "agent for combating pollution" is understood to mean any compound capable of trapping ozone, mono-or polycyclic aromatic compounds, such as benzopyrene, and/or heavy metals, such as cobalt, mercury, cadmium and/or nickel. The term "agent for combating free radicals" is understood to mean any compound capable of trapping free radicals.

Mention may in particular be made, as ozone-trapping agents which can be used in the composition according to the invention, of vitamin C and its derivatives, including ascorbyl glucoside; phenols and polyphenols, in particular tannins, ellagic acid and tannic acid; epigallocatechin and the natural extracts comprising it; extracts of olive tree leaf; extracts of tea, in particular of green tea; anthocyans; extracts of rosemary; phenol acids, in particular chlorogenic acid; stilbenes, in particular resveratrol; sulphur-comprising amino acid derivatives, in particular S-carboxymethylcysteine; ergothioneine; N-acetyl-cysteine; chelating agents, such as N,N'-bis (3,4,5-trimethoxybenzyl)ethylenediamine or one of its salts, metal complexes or esters; carotenoids, such as crocetin; and various starting materials, such as the mixture of arginine, histidine ribonucleate, mannitol, adenosine triphosphate, pyridoxine, phenylalanine, tyrosine and hydrolysed RNA sold by Laboratoires S'robiologiques under the trade name CPP LS 2633-12F®, the water-soluble fraction of maize sold by Solabia under the trade name Phytovityl®, the mixture of extract of fumitory and extract of lemon sold under the name Unicotrozon C_490 by Induchem, and the mixture of extracts of ginseng, of apple, of peach, of wheat and of barley sold by Provital under the trade name Pronalen Bioprotect®.

Mention may in particular be made, as agents which trap mono- or polycyclic aromatic compounds which can be used in the composition according to the invention, of tannins, such as ellagic acid; indole derivatives, in particular indole-3-carbinol; extracts of tea, in particular of green tea; extracts of water hyacinth or *Eichhornia crassipes*; and the water-soluble fraction of maize sold by Solabia under the trade name Phytovityl®.

Finally, mention may in particular be made, as agents which trap heavy metals which can be used in the composition according to the invention, of chelating agents, such as EDTA, the pentasodium salt of ethylenediaminetetramethylenephosph0j acid, and N,N'-bis (3,4,5-trimethoxybenzyl)ethylenediamine or one of its salts, metal complexes or esters; phytic acid; chitosan derivatives; extracts of tea; in particular of green tea; tannins, such as ellagic acid; sulphur-comprising amino acids, such as cysteine; extracts of water hyacinth (*Eichhornia crassipes*); and the water-soluble fraction of maize sold by Solabia under the trade name Phytovityl®.

The agents for combating free radicals which can be used in the composition according to the invention comprise, in addition to some agents for combating pollution mentioned above, vitamin E and its derivatives, such as tocopheryl acetate; bioflavonoids; coenzyme Q10 or ubiquinone; certain enzymes, such as catalase, superoxide dismutase and wheat germ extracts comprising it, lactoperoxidase, glutathione peroxidase and quinone reductases; glutathione; benzylidenecamphor; benzylcyclanones; substituted naphthalenones; pidolates; phytanthriol; 7-oryzanol; guanosine; lignans; and melatonin.

Soothing agents Mention may be made, as soothing agents which can be used in the composition according to the invention, of: pentacylic triterpenes and plant extracts (for example, *Glycyrrhiza glabra*) comprising them, such as 3-glycyrrhetinic acid and its salts and/or its derivatives (glycyrrhetinic acid monoglucuronide, stearyl glycyrrhetinate or 3-stearoyl-oxyglycyrrhetic acid), ursolic acid and its salts, oleanolic acid and its salts, betulinic acid and its salts, extracts of plants, such as *Paeonia suffruticosa* and/or *lactiflora, Laminaria saccharina, Boswellia serrata, Centipeda cunninghamii, Helianthus annuus, Linum usitatissimum, Cola nitida, Epilobium angustifolium, Aloe vera* or *Bacopa monnieri*, salts of salicylic acid and in particular zinc salicylate, canola oil, bisabolol, camomile extracts, allantoin, S' pivital EPC (phosphoric diester of vitamin E and C) from Seppic, omega-3 unsaturated oils, such as musk rose, blackcurrant seed, echium or fish oils, plankton extracts, capryloylglycine, Seppicaim VG (sodium palmitoylproline and *Nymphaea alba*) from Seppic, tocotrienols, piperonal, an extract of clove, phytosterols, cortisone, hydrocortisone, indomethacin and betamethasone.

It is to be understood that any composition as herein described may be used in the methods of this invention, as well.

In some embodiments, this invention provides a method of improving a skin characteristic, the method comprising contacting a skin surface of a subject with a composition comprising a coral of this invention. In some embodiments, the method further comprises contacting the skin with a composition further comprising a chelator, as herein described, and in some embodiments, further comprising other agents, which directly or indirectly improve a skin characteristic.

In some embodiments, this invention provides a method of treating a skin disease, disorder or condition, the method comprising contacting an affected skin surface of a subject with a composition comprising a coral of this invention. In some embodiments, the method further comprises contacting the affected skin with a composition further comprising a chelator, as herein described, and in some embodiments, further comprising other agents, which directly or indirectly improve a skin characteristic. In some embodiments, the term "affected skin" refers to diseased skin. In some embodiments, the term "affected skin" refers to skin, which shows indications of a skin disorder or condition. In some embodiments, the term "affected skin" refers to skin, which is in any way altered from a "normal" or "healthy" appearance. In some embodiments, the term "affected skin" refers to skin, which can be identified as prone to, or subject to a skin disease, disorder or condition.

In some embodiments, the skin disease, disorder or condition is a neoplasia, or preneoplastic lesion or cells, for example, melanoma, basal cell carcinoma, etc. In some embodiments, the skin disease, disorder or condition is a result of infection, for example, with *leishmania, mycobacteria, streptococcus, staphylococcus*, herpes virus, varicella virus, or others. skin disease, disorder or condition is a result of an inflammatory response, for example in response to allergy or exposure to an infection, an irritant, or others.

In some embodiments, the skin disease, disorder or condition is chronologically or hormonally-aged or photo-aged skin, such as fine lines, wrinkles, and sagging skin, and other conditions due to a progressive degradation of the dermal-epidermal junction (DEJ) and of the cell-cell cohesion in the epidermis. In some embodiments, such disease, disorder or condition may be treated with a topical composition comprising the coral and optionally chelator, as described herein, and in some embodiments, is formulated as a cosmetic product for the face and/or body.

EXAMPLES

Materials & Methods

Materials $^{45}CaCl_2$ was obtained from NEN Life Science (Boston, Mass., USA), and calcein-AM was obtained from Molecular Probes Inc., Eugene, Oreg., USA.

Matrix Preparation

Two biomaterial derivatives were prepared, one from the hydrocoral *M. dichotoma* (designated MIL) and the other, for purposes of comparison, from scleractinian coral *P. lutea*—(designated POR). Colonies of *M. dichotoma* were collected from the shallow seawater zones adjacent to the Interuniversity Institute of Marine Science (IUD in Eilat, Israel, at depths of 6-8 meters. Each colony was cut into fragments and glued with epoxy resin into the tops of PVC tubes. After an adjustment period of 3 months, cloned fragments were transferred to a laboratory tank system. POR were prepared from cores drilled out from long-lived massive colonies.

Both types of skeleton were cut into blocks and bleached using a commercial hypochloride solution. After this preliminary cleaning process, samples were rinsed with distilled water and air-dried. Pieces that were 0.5 mm thick and approximately 0.5 $cm^2$ were polished using an 8" grinder (SBT 900, South Bay Technologies, San Clemente, Calif.) followed by manual polishing. The final matrices used were 2×2×0.5 mm for histochemical staining and 4×4×0.7 mm for other assays. The samples were rinsed with NaOH (2 N) in order to remove organic residues and with $H_2O_2$ (Gerdrogen 30% wt, Riedel-de Haen, Germany) in order to remove inorganic residues (each solution for 10 min). The samples were autoclaved (121° C., 40 min) and oven dried overnight at 80° C. Microcolonies were transferred to tank systems and incubated with $^{45}Ca^{2+}$ and calcein for 48 hours.

Preparation of Mesenchymal Stem Cells

MSCs from a cell line origin (*Mus-musculus*; ATTC/CRL-12424) were seeded at a concentration of 6400 cell/matrix in Dulbecco's modified Eagle's medium (DMEM) supplemented with 4.5 g/L D-glucose, 1.5 g/L sodium bicarbonate (Sigma-Aldrich, Rehovot, Israel), 1 mM sodium pyruvate, 10% (v/v) fetal calf serum, 1% LGlutamin, and 1% Pen-Strep-Nystatin solution (all from Biological Industries, Beit Haeemek, Israel, except as noted). No osteoinducing supplements were added. Cell cultures were incubated in a humidified atmosphere of 5% $CO_2$ at 37° C. The medium was replaced every 2 days. MSCs were seeded onto labeled biomatrices and cultured with low calcium or control medium.

Scanning Electron Microscopy

After fixation (30 min, 37° C.) in 2% paraformaldehyde and 2.5% glutaraldehyde in 0.1 M phosphate buffer, seeded samples were rinsed twice in PBS for 10 min. Samples were then washed five times for 15 min each in a series of increasing ethanol concentrations (50, 75, 90, and 95% v/v) and three times for 10 min each in analytic ethanol. After ethanol washes, samples were rinsed in a series of different Hexamethyldisilazane (HMDS) concentrations (33.3, 50, and 66.6% v/v in analytic ethanol) and three times in 100% RMDS for 1 min each. Samples were dried overnight. Cells and tissue morphology characterization was performed by means of SEM on a Quanta 200 ESEM/SEM, FEI instrument (Phillips, Bothell, Wash.) operating with beam energies of 6-25 kV. Samples were glued with conducting paste to mounting stubs, which were then sputter-coated with gold-palladium.

Light Microscopy

Light inverted microscopy (TE300, Nikon, Tokyo, Japan) follow-up was conducted every day. Samples were rinsed with phosphate-buffered saline (PBS, Biological Industries), fixed with formaldehyde solution (12%), and rinsed again at room temperature. The samples were stained with 5% trypan blue dye (Biological Industries) for 5 min at room temperature and then rinsed with distilled water.

Cell Density Analysis

Images were acquired using an Axiovert-200 (Zeiss, Germany) inverted microscope equipped with X20 Plan-Neofluar (N.A. 0.50) and X40 LD-Acrhoplan objectives (N.A. 0.60) and a cooled CCD camera (SensiCam, PCO, USA) controlled by Metamorph (version 6.2, Universal Imaging, Downingtown, Pa.). Regions along the polished surface showing 40, 6-diaminidino-2-phenylindole (DAPI)-positive nuclei were photographed in single planes, 1-2 mm from the crystalline surface. Cells were counted manually, and the numbers were averaged and interpolated for 1 $mm^2$ of crystalline surface.

Calcein Assay

Confocal Microscopy and Image Analysis

Ten micron sections were cut and immediately loaded onto glass slides and were examined using a Leica DMIRBE inverted microscope coupled to a Leica TCS SP confocal system (Leica Microsystems, Sydney, Australia). Cells were excited at 488 nm and fluorescence collected using emission windows set at 500-540 nm. All signals collected were adjusted to remain within the linear range of the detectors. Images were collected using the TCS NT software (Leica Microsystems, Sydney, Australia). Differences between treatments were analyzed using One-Way ANOVA (jmp software, v3.0.2, SAS Institute Inc.). Images incorporated into figures were exported as TIFF files and prepared for publication by Adobe Photoshop v 5.0 software.

Calcification Assay ($^{45}Ca$ Accumulation)

Coral (~20 mg) was sliced and incubated in 1 mL Krebs-Henseleit (K-H) solution (in mmol/L: 118 NaCl, 4.7 KCl, 1.3 $CaCl_2$, 1.2 $KH_2PO_4$, 1.2 $MgSO_4$, 25 $NaHCO_3$, and 5 glucose; pH 7.2) with 37 kBq/mL of $^{45}CaCl_2$. The reaction was stopped by the addition of ice-cold K-H solution. The coral was dissolved and DNA concentration was determined by spectrophotometry at $OD_{260}$. $^{45}Ca^{2+}$ radioactivity was measured by β-scintillation counting (LS 6500; Beckman).

DNA Analysis

DNA concentration was determined using the Pico-Green dsDNA Quantification kit (Molecular Probes, Eugene, Oreg.). One day before the analysis was carried out, each sample (n=5 for each biomatrix) was transferred into individual 24-well plates in 1 mL serum-free medium. Samples were sonicated for 1 min, and from each well, 50 µL of the DNA solution were transferred to a 96-well fluorescent plate. 100 µl, of 1×TE solution (20 mM Tris-HCl, 20 mM EDTA, pH 7.5 buffer) was added to each well, followed by 150 µL of PicoGreen solution (diluted 1:200 with 1×TE solution) and incubated at room temperature for 5 min in the dark. Excitation was read at 480 nm and emission at 520 nm using a fluorometer (Cary Eclipse Fluorecence spectrometer, Varian, Oxford, United Kingdom). DNA standard curve was plotted using standard bacteriophage lambda DNA.

Cadherin-11 RT-PCR and Northern Blot Analysis.

RT-PCR was performed using 0.2 mg (β-actin) or 1.0 mg (cadherin-11) of total RNA, isolated using the guanidinium isothiocyanate method (Sambrook et al, Molecular Cloning: A Laboratory Manual. Cold Spring Harbor, N.Y.: Cold Spring Harbor Laboratory, 1989). The following primers were used: (β-actin upstream, 5'-TGACGGGGTCACCCA-CACTGTGCCCATCTA-3'; β-actin downstream, 5'-CTA-GAAGCATTTGCGGTGGACGATGGAGGG-3'; cadherin-11 wildtype upstream, 5'-ACCAGATGTCTGTGTCAGA-3'; cadherin-11 wild-type downstream, 5'GTCATCCTTGT-CATCTGCA-3'; cadherin-11 variant upstream, 5'-CGC-CGCGGATCCTTAATGGAACCCCCCTCTC-3'; and cadherin-11 variant downstream, 5'-CCGCCGGAATTCTCCGTAAGTGTGGTTG-GACTCTC-3'. First-strand synthesis with the downstream primer and MMLV-RT (Gibco/BRL) was followed by PCR using Taq polymerase (Life Technologies, Inc.) after adding the upstream primer. The following cycling parameters were used: cadherin-11 wild type, 94° C. for 30 s, 55° C. for 30 s, 72° C. for 2 min, 35 cycles; cadherin-11 variant, 94° C. for 1.5 min, 55° C. for 2 min, 72° C. for 3 min, 35 cycles. Both parameters could be used for β-actin. The PCR product was run on a 1% agarose gel. The following fragments were amplified: β-actin, a 661-bp fragment that spans an intron to rule out genomic contamination; cadherin-11 wild type, a 742-bp fragment from a region encoding part of the extracellular domain; cadherin-11 variant, a 194-bp fragment that encodes most of the COOH-terminal 75 amino acids present only in the variant (Okazaki et al., J. Biol. Chem., 269: 12092-12098, 1994).

Twenty μg of total RNA were separated on a 1% agarose gel and transferred to a nylon membrane (Boehringer Manheim; Sambrook et al, 1989). A 1.6-kb fragment of the cadherin-11 cDNA was labeled using $^{32}$P-labeled dCTP and used to probe the blot. The blot was hybridized at 50° C. overnight, then washed three times in 2% SSC at 55° C. and 65° C. (last wash). The labeled bands were visualized using a phosphorimager. The nylon was then reprobed for GAPDH as a control.

N-Cadherin RNA Extraction and Northern Blot Analysis

Total RNA was prepared from cultured cells by acid guanidinium thiocyanate-pheno-chloroform extraction. Twenty micrograms of each RNA sample were separated by electrophoresis in 1% agarose gel containing 1.85% formaldehyde and transferred onto a Hybond N+ nylon membrane (Amersham Life Science, Arlington Heights, Ill.). N-cadherin mRNA was detected by Northern blot analysis as in Reid and Hemperly (Nucleic Acids Research 1990, 18:5896). Probes were random-primed with labeled-$^{32}$PdCTP (Amersham). Membranes were prehybridized for 18 hours at 42° C. in a 6×SSC buffer consisting of 0.05 mol/L NaH$_2$PO$_4$, 5×Denhardt's (50×=% Ficoll, 1% polyvinylpyrrolidone, 1% BSA), 1% SDS, 50% formamide, and 10 μg/ml salmon sperm DNA. A denatured probe was added to blots and hybridized overnight. Blots were sequentially washed for 30 minutes at 65° C. using the following conditions: 2×SSC/0.1% SDS, 0.3× SSC/0.5% SDS, and 0.1×SSC/1.0% SDS. Blots were then exposed to X-OMAT AR film (Kodak). Normalization for loading was compared to hybridization of a 1.2-kb PstI fragment of human GAPDH (GenBank Accession J04038).

Example 1

Growth of Mesenchymal Stem Cells Grown on *Porites Lutea*

In order to determine calcium-mediated effects of coral on mesenchymal stem cell (MSC) growth, Scanning Electron Micrographs (SEMs) were taken of coral seeded with MSCs with and without incubation with a calcium chelator. SEMs showed increasing MSC density in both porites lutea (POR) and gold-coated POR (GCPOR) biomatrices at 1, 4, and 7 days post seeding (FIGS. 2A and 2B). Incubation with the calcium chelator, EGTA further increased local cell density (FIGS. 2Aj, 2Al).

Example 2

Calcium Uptake of Mesenchymal Stem Cells Grown on *Porites Lutea*

Figure 3:
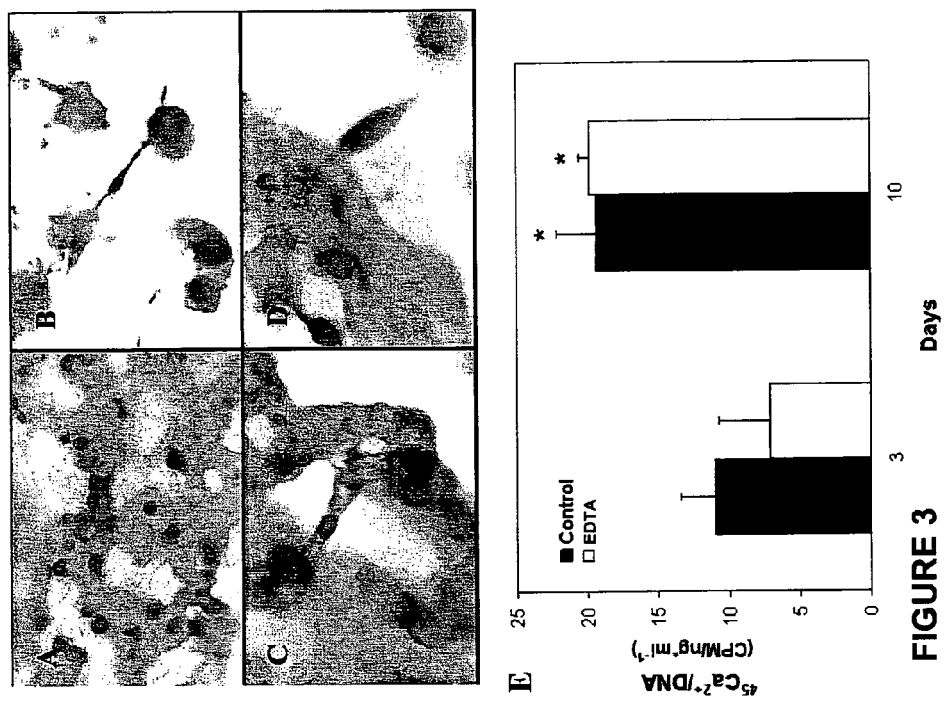
FIG. 3 presents calcium measurements in mesenchymal stem cells (MSCs) seeded on biolabeled biomatrices. (A) Fluorescent microscopy photographs showing calcein-labeled biomatrix (B-D) calcium uptake by MSCs 7 days post seeding; Cell nuclei are shown. Photograph magnifications: (A and B) X200; (C and D) X400. (E) $^{45}Ca^{2+}$ measurement in MSCs seeded on biolabled biomatrices, 3 and 10 days post seeding. Results are normalized to DNA concentrations and shown as mean±SD. (Student t-test: (*)–p<0.01.

Calcein labeling of MSCs seeded on biolabeled biomatrices showed calcium uptake from the biomatrix at 7 days post-seeding (FIGS. 3B-D). There was a greater increase in labeled calcium uptake within MSCs at 10 days post-seeding as compared to 3 days post-seeding in control and EGTA-treated matrices (FIG. 3E).

Example 3

Cadherin Changes in Mesenchymal Stem Cells Grown on *Porites Lutea*

Cadherin-11 (Cad-11) and N-cadherin (N-Cad) mRNA levels in MSCs increased as a function of days post-seeding, with Cad-11 and N-Cad peak expression at 21 days in non-gold-coated and 14 days in gold-coated porites lutea. Cad-11 expression was higher in non-gold-coated porites lutea, while N-Cad expression was higher in gold-coated porites lutea (FIGS. 4A-B).

What is claimed:

1. A method of inducing or enhancing bone or cartilage formation or a combination thereof in a subject comprising administering to said subject a composition comprising: coral seeded with precursor cells selected from mesenchymal stem cells, chondrocytes and osteoblasts, wherein said coral is seeded with said cells in culture in the presence of a chelator for a period of time sufficient to seed said cells in said coral and wherein the cell density of said cells is higher than that of the same type of coral seeded with the same type of cells in culture in the absence of the chelator.

2. The method of claim 1, wherein said coral is from the *Porites* species, *Millepora* species or *Acropora* species.

3. The method of claim 2, wherein said coral is *Porites lutea*.

4. The method of claim 2, wherein said coral is *Millepora dichotoma*.

5. The method of claim 2, wherein said coral is *Acropora grandis*.

6. The method of claim 1, wherein said chelator is a calcium chelator, which is EDTA or calcein.

7. The method of claim 1, wherein said chelator serves to eliminate diffuse calcium signaling.

8. The method of claim 1, wherein calcium released from said coral stimulates precursor cell seeding, bone formation, cartilage formation or a combination thereof.

9. The method of claim 1, wherein said coral is seeded with said precursor cell in serum-free medium.

10. The method of claim 1, wherein said precursor cells are autologous, syngeneic, or allogeneic.

11. The method of claim 1, wherein said subject has bone or cartilage infirmity.

12. The method of claim 1, wherein said composition is administered to a site of bone or cartilage infirmity, or a combination thereof.

13. The method of claim 1, wherein said subject suffers from bone loss, cartilage defects, osteochondral defects or osteochondrytis.

14. The method of claim 1, wherein said period of time sufficient to seed said precursor cells in said coral is up to 72 hours.

15. The method of claim 1, wherein said subject has osteoporosis.

16. The method of claim 1, wherein said subject has Paget's disease, fibrous dysplasia or osteodystrophy.

17. The method of claim 1 comprising the additional step of seeding said coral with a precursor cell in culture in the presence of a chelator, prior to said administrating.

18. The method of claim 17 wherein after seeding the cells are cultured up to 24 hours before said administrating.

19. A method of inducing or enhancing bone or cartilage formation or a combination thereof in a subject comprising:
    seeding coral with precursor cells selected from mesenchymal stem cells, chondrocytes and osteoblasts,
    culturing the seeded coral in the presence of a chelator for not more than 72hours,
    and administering to said subject a composition comprising said cultured seeded coral.

20. The method of claim 19, wherein said coral is from the *Porites* species, *Millepora* species or *Acropora* species.

21. The method of claim 20, wherein said coral is *Porites lutea*.

22. The method of claim 20, wherein said coral is *Millepora dichotoma*.

23. The method of claim 20, wherein said coral is *Acropora grandis*.

24. The method of claim 19, wherein said chelator is a calcium chelator, which is EDTA or calcein.

25. The method of claim 19, wherein said chelator serves to eliminate diffuse calcium signaling.

26. The method of claim 19, wherein calcium released from said coral stimulates precursor cell seeding, bone formation, cartilage formation or a combination thereof.

27. The method of claim 19, wherein said coral is seeded with said precursor cell in serum-free medium.

28. The method of claim 19, wherein said precursor cells are autologous, syngeneic, or allogeneic.

29. The method of claim 19, wherein said subject has bone or cartilage infirmity.

30. The method of claim 19, wherein said composition is administered to a site of bone or cartilage infirmity, or a combination thereof.

31. The method of claim 19, wherein said subject suffers from bone loss, cartilage defects, osteochondral defects or osteochondrytis.

* * * * *